United States Patent
Cosse

(10) Patent No.: US 8,337,198 B2
(45) Date of Patent: Dec. 25, 2012

(54) REUSABLE MULTI-PIECE ORTHODONTIC APPLIANCES

(76) Inventor: Christopher C. Cosse, Shreveport, LA (US)

(*) Notice: Subject to any disclaimer, the term of this patent is extended or adjusted under 35 U.S.C. 154(b) by 30 days.

(21) Appl. No.: 12/910,974

(22) Filed: Oct. 25, 2010

(65) Prior Publication Data

US 2011/0039224 A1  Feb. 17, 2011

Related U.S. Application Data

(63) Continuation of application No. 11/260,074, filed on Oct. 26, 2005, now Pat. No. 7,819,660.

(51) Int. Cl.
*A61C 3/00* (2006.01)
(52) U.S. Cl. .................................................. 433/8
(58) Field of Classification Search ............... 433/8–17
See application file for complete search history.

(56) References Cited

U.S. PATENT DOCUMENTS

| | | | |
|---|---|---|---|
| 1,280,628 A | 10/1918 | Angle | |
| 1,821,171 A | 9/1931 | Atkinson | |
| 2,921,371 A | 1/1960 | Wallshein | |
| 3,421,221 A * | 1/1969 | Silverman et al. | 433/8 |
| 3,435,527 A | 4/1969 | Kesling | |
| 3,464,113 A | 9/1969 | Silverman et al. | |
| 3,597,845 A | 8/1971 | Russ | |
| 3,772,787 A | 11/1973 | Hanson | |
| 3,946,488 A | 3/1976 | Miller et al. | |
| 4,077,126 A | 3/1978 | Pletcher | |
| 4,134,208 A | 1/1979 | Pearlman | |
| 4,144,642 A | 3/1979 | Wallshein | |
| 4,171,568 A | 10/1979 | Forster | |
| 4,197,642 A | 4/1980 | Wallshein | |
| 4,212,638 A | 7/1980 | Korn | |
| 4,248,588 A | 2/1981 | Hanson | |
| 4,249,897 A | 2/1981 | Anderson | |
| 4,302,532 A | 11/1981 | Wallshein | |
| 4,371,337 A | 2/1983 | Pletcher | |
| 4,419,078 A | 12/1983 | Pletcher | |
| 4,487,581 A | 12/1984 | Adler | |
| 4,492,573 A | 1/1985 | Hanson | |
| 4,496,318 A | 1/1985 | Connelly, Jr. | |
| 4,531,911 A | 7/1985 | Creekmore | |
| 4,559,012 A | 12/1985 | Pletcher | |
| 4,561,844 A | 12/1985 | Bates | |
| 4,597,739 A | 7/1986 | Rosenberg | |
| 4,614,497 A | 9/1986 | Kurz | |
| 4,634,661 A | 1/1987 | Cavallaro | |
| 4,655,708 A | 4/1987 | Fujita | |
| 4,698,017 A | 10/1987 | Hanson | |
| 4,712,999 A | 12/1987 | Rosenberg | |

(Continued)

*Primary Examiner* — Heidi M Eide
(74) *Attorney, Agent, or Firm* — DASCENZO Intellectual Property Law, P.C.

(57) ABSTRACT

Multi-piece, reusable orthodontic appliances that include a support assembly to be bonded to a tooth and a corrective assembly adapted to receive an archwire and direct corrective forces exerted by the archwire to the tooth. The support assembly is releasably engaged with the corrective assembly, such as with coupling portions that disengage responsive to a force applied to the corrective assembly exceeding a predetermined value, such as less than a force sufficient to debond the support assembly from the tooth. In response to such a force, the corrective assembly disengages from the support assembly, rather than the appliance debonding from the tooth. Self-release assemblies for use with a corrective orthodontic bracket, including either a support assembly or a corrective assembly, and an engagement assembly configured to disengage as described above, may allow a conventional set of orthodontic hardware to be retrofitted with a self-release feature.

24 Claims, 11 Drawing Sheets

U.S. PATENT DOCUMENTS

| | | | |
|---|---|---|---|
| 4,786,242 A | 11/1988 | Barsk | |
| 4,878,840 A | 11/1989 | Reynolds | |
| 5,032,080 A | 7/1991 | Hakansson et al. | |
| 5,044,945 A | 9/1991 | Peterson | |
| 5,064,369 A | 11/1991 | Kawaguchi | |
| 5,094,614 A | 3/1992 | Wildman | |
| 5,263,859 A | 11/1993 | Kesling | |
| 5,322,435 A | 6/1994 | Pletcher | |
| 5,356,288 A | 10/1994 | Cohen | |
| 5,366,372 A | 11/1994 | Hansen et al. | |
| 5,439,379 A | 8/1995 | Hansen | |
| 5,562,444 A | 10/1996 | Heiser et al. | |
| 5,711,666 A | 1/1998 | Hanson | |
| 5,746,593 A | 5/1998 | Forster | |
| 5,857,850 A | 1/1999 | Voudouris | |
| 5,902,104 A | 5/1999 | Yamada | |
| 6,071,119 A | 6/2000 | Christoff et al. | |
| 6,139,317 A | 10/2000 | Goldschmied | |
| 6,142,775 A | 11/2000 | Hansen et al. | |
| 6,193,508 B1 | 2/2001 | Georgakis | |
| 6,220,857 B1 | 4/2001 | Abels | |
| 6,264,469 B1 | 7/2001 | Moschik | |
| 6,302,688 B1 | 10/2001 | Jordan et al. | |
| 6,358,045 B1 | 3/2002 | Farzin-Nia et al. | |
| 6,582,226 B2 | 6/2003 | Jordan et al. | |
| 6,632,088 B2 | 10/2003 | Voudouris | |
| 6,655,957 B2 | 12/2003 | Abels et al. | |
| 6,659,766 B2 | 12/2003 | Abels et al. | |
| 7,083,412 B1 | 8/2006 | Karapetyan | |
| 2002/0110777 A1 | 8/2002 | Abels et al. | |
| 2003/0003415 A1 | 1/2003 | Kim et al. | |
| 2003/0198913 A1 | 10/2003 | Cinader, Jr. et al. | |
| 2004/0185410 A1 | 9/2004 | Lai | |
| 2005/0244776 A1* | 11/2005 | Abels et al. | 433/10 |
| 2006/0014116 A1 | 1/2006 | Maijer et al. | |
| 2006/0292517 A1 | 12/2006 | Smith | |
| 2008/0241782 A1 | 10/2008 | Abels et al. | |

* cited by examiner

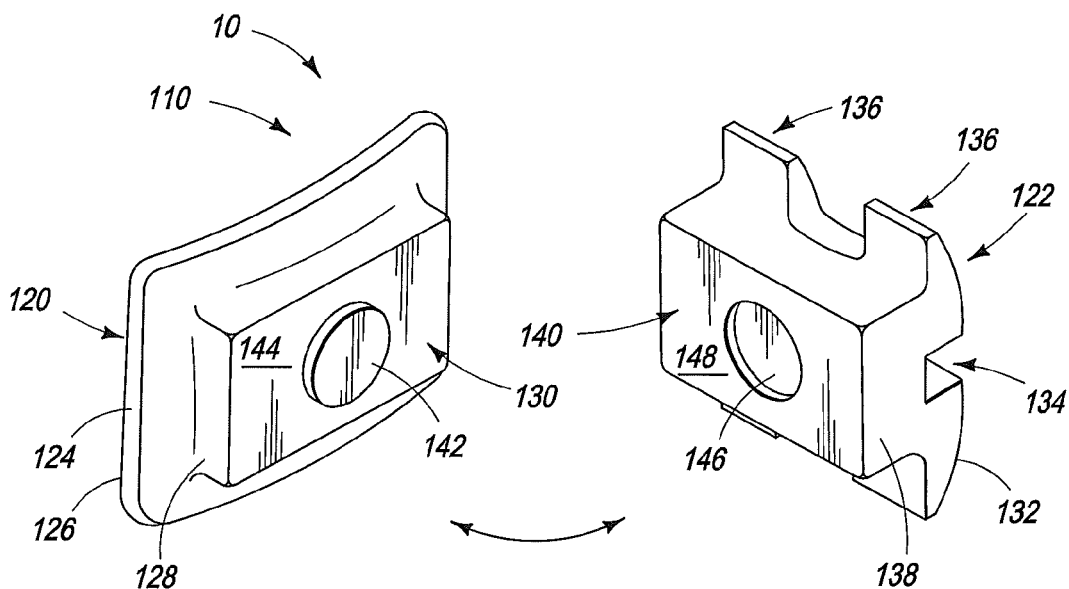
FIG. 15
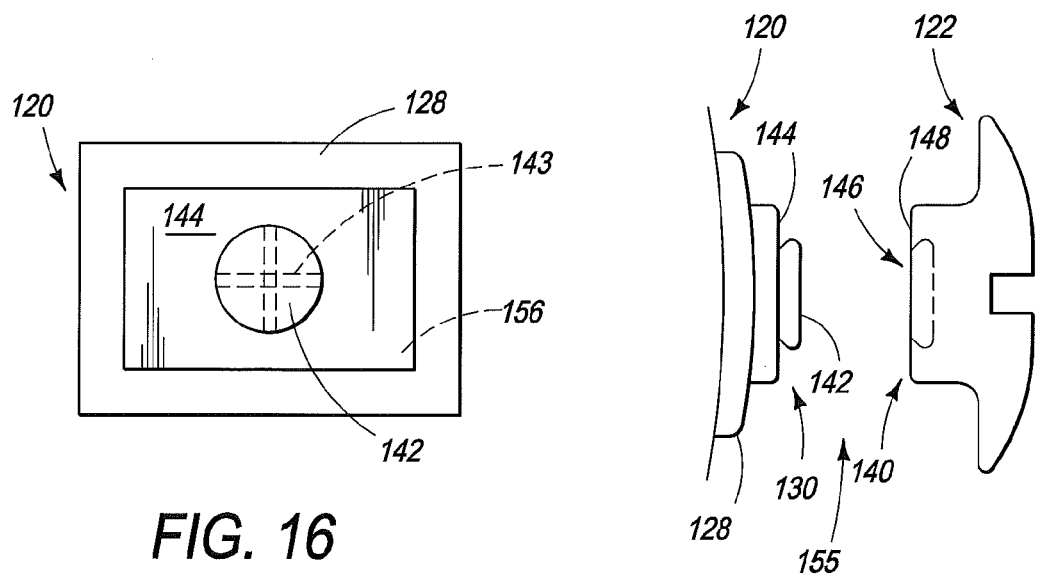
FIG. 16
FIG. 17
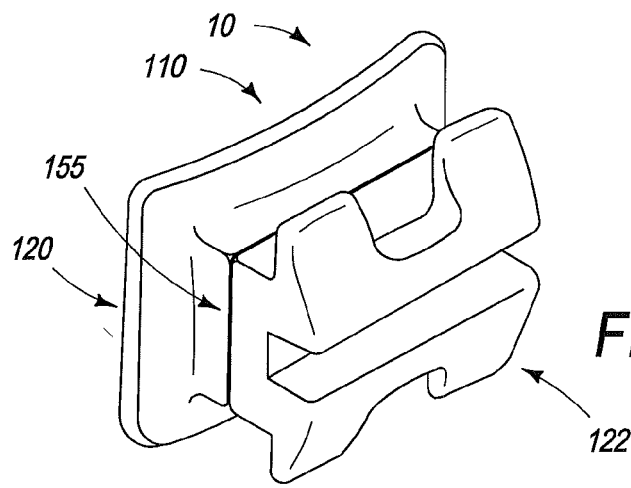
FIG. 18

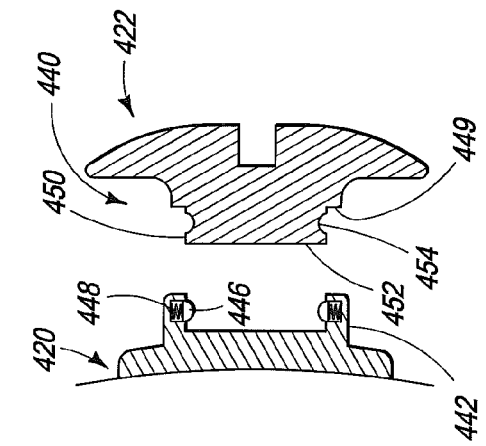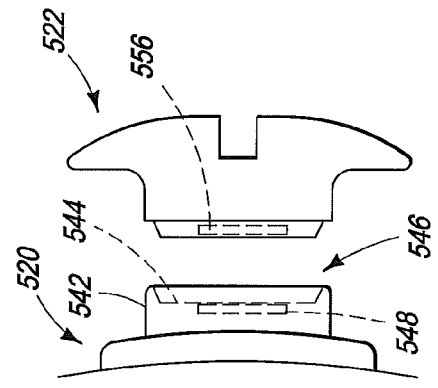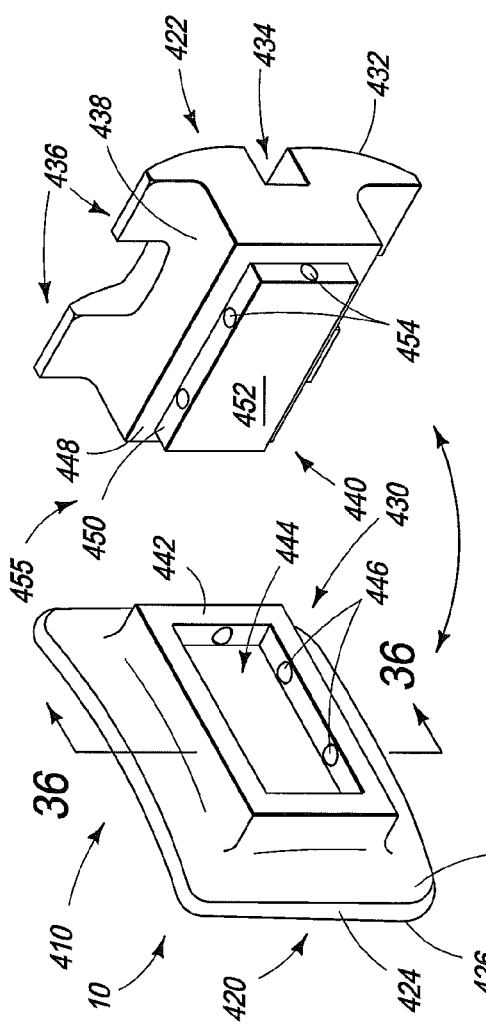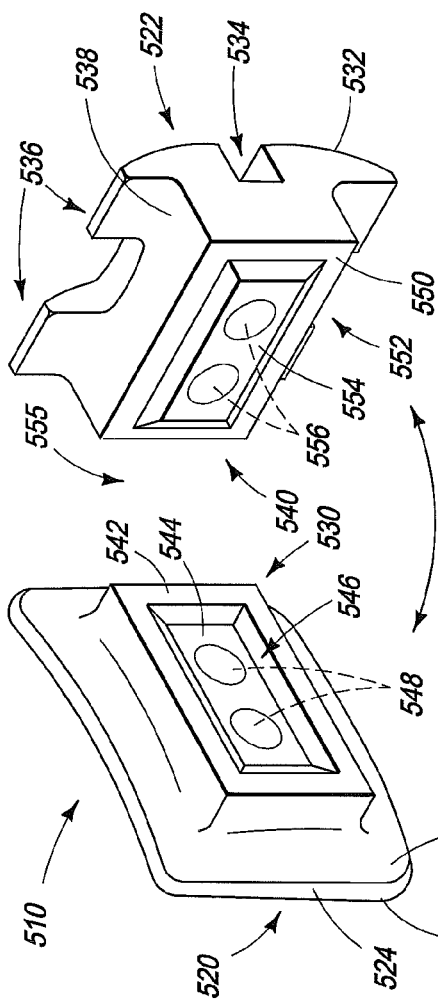

US 8,337,198 B2

REUSABLE MULTI-PIECE ORTHODONTIC APPLIANCES

RELATED APPLICATION

The present application is a continuation patent application that claims priority under 35 U.S.C. §120 to U.S. patent application Ser. No. 11/260,074, which is entitled "Reusable Multi-Piece Orthodontic Appliances," which was filed on Oct. 26, 2005, and which issued on Oct. 26, 2010 as U.S. Pat. No. 7,819,660. The complete disclosure of the above-identified patent application is hereby incorporated by reference for all purposes.

TECHNICAL FIELD

The present disclosure relates generally to orthodontic hardware, and more particularly to orthodontic devices configured to direct corrective forces from an archwire to a tooth.

BACKGROUND OF THE DISCLOSURE

Orthodontic brackets are typically small, slotted devices for use during orthodontic treatment. The brackets are usually configured for attachment to the front surfaces of teeth, either by directly cementing the bracket to a tooth surface or by bonding the bracket to a metal band that encircles the tooth. The slots in the brackets are generally horizontally disposed, and configured to receive an archwire. Traditionally, an archwire is a resilient, curved piece of wire that may be bent or twisted prior to installation, and then seated in the bracket slots. The restoring forces exerted by the archwire are directed to the teeth by the orthodontic brackets in order to urge the teeth into a correct, or desired, alignment.

The archwire may be secured in the bracket slots by several different means, depending on the bracket configuration. For example, a "ligating" bracket typically requires fastening means, such as ligature wires or elastic bands, that are tied around tie wings on the bracket body to secure the archwire in place. A "self-ligating" bracket, on the other hand, typically includes a clamp or other self-locking mechanism, such as a closeable bracket slot, that allows such a bracket to retain the archwire without requiring the use of ligatures.

Bonding agents that are used to cement a bracket to the tooth typically establish a bond that is of sufficient strength to maintain securely the bracket on the tooth. To avoid damage to the tooth, the bond achieved by some bonding agents may release the bracket from the tooth when a threshold mechanical force is applied to the bracket, such as the impact of a sudden, direct force, shear stress from chewing food, biting upon a hard object, and so forth. However, even though such bonding agents may help to avoid direct damage to teeth by allowing the bracket to debond whenever such a force is applied, much orthodontic maintenance time is spent reattaching brackets to teeth. As such, in addition to patient discomfort and lengthy treatment sessions necessitated by inadvertent debonding of brackets from teeth, repeated bonding and debonding may abrade, deteriorate, or otherwise damage the tooth surface.

BRIEF DESCRIPTION OF THE DRAWINGS

FIG. 15 is an exploded isometric view showing a first embodiment of a multi-piece, reusable orthodontic appliance according to the present disclosure.

FIG. 16 is a front elevation view of the support assembly of the orthodontic appliance of FIG. 15.

FIG. 17 is an exploded side elevation view of the orthodontic appliance of FIG. 15.

FIG. 18 is an assembled isometric view of the orthodontic appliance of FIG. 15, with the corrective assembly engaged with the support assembly.

FIG. 35 is an exploded isometric view of another embodiment of a multi-piece, reusable orthodontic appliance according to the present disclosure.

FIG. 36 is a cross-sectional side elevation view of the orthodontic appliance of FIG. 35 along the lines 36-36 in FIG. 35.

FIG. 37 is an exploded isometric view of another embodiment of a multi-piece, reusable orthodontic appliance according to the present disclosure.

FIG. 38 is an exploded side elevation view of the orthodontic appliance of FIG. 37.

DETAILED DESCRIPTION AND BEST MODE OF THE DISCLOSURE

Figure 1:
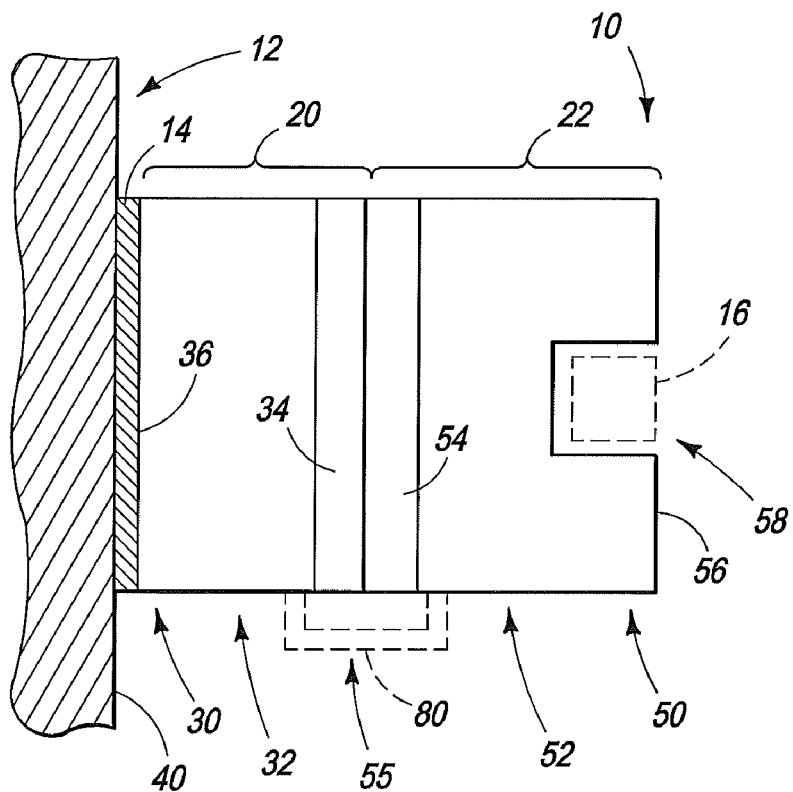
FIG. 1 is a schematic diagram showing various components of an illustrative example of a multi-piece, reusable orthodontic appliance according to the present disclosure.

Various exemplary embodiments of multi-piece, reusable orthodontic appliances are presented herein. The embodiments generally include a support assembly that may be bonded to a tooth, and a corrective assembly that is configured to receive an archwire and direct corrective forces exerted by the archwire to a tooth. The support assembly may be configured to be releasably attached to, or otherwise engaged with, the corrective assembly, such as by means of corresponding coupling portions on at least one of the assemblies, and in some embodiments, on both assemblies. The coupling portion(s) may be configured to disengage responsive to a force applied to the corrective assembly, such as a force that exceeds a predetermined value. For example, if the predetermined value is less than the force sufficient to debond the support assembly from the tooth, the coupling portions may allow the corrective assembly to break away from the support assembly responsive to the aforementioned force, rather than permit such a force to cause the orthodontic appliance to break away from the tooth.

Moreover, in at least some embodiments, the coupling portions may be configured to be reusable after being disengaged, thereby allowing repeated engagement and disengagement of the coupling portions, such as during installation and throughout the duration of orthodontic treatment, without destruction or deterioration to any of the components of the appliance caused by engaging or disengaging the coupling portions. For example, each of the first and second coupling assemblies may be adapted to remain structurally intact upon engagement and disengagement.

Although other configurations are possible and are within the scope of the present disclosure, some embodiments of an orthodontic appliance include a support assembly and a corrective assembly, the support assembly further including a tooth engaging portion adapted to bond the support assembly to a tooth, a support portion extending from the tooth engaging portion, and a first coupling portion; and the corrective assembly further including a wire engaging portion adapted to receive an archwire, a base portion extending from the wire engaging portion, and a second coupling portion on the base portion adapted to releasably engage the first coupling portion. In such embodiments, the first and second coupling portions are configured to disengage responsive to a force applied to the corrective assembly that exceeds a predetermined value.

Some embodiments or orthodontic appliances according to the present disclosure may include an alignment feature, such as coupling portions that are configured to engage only when urged together in one or more predetermined orientations. Such an alignment feature may reduce the time required to properly couple the portions together during a session of orthodontic maintenance, such as by facilitating correct alignment of a corrective assembly with a support assembly. Such a feature may optionally allow an orthodontic patient to correctly re-engage a corrective assembly that has become disengaged from a support assembly without having to consult an orthodontist. Further, an alignment feature may assist, or guide, alignment in a desired orientation of a corrective assembly that is configured to direct corrective forces differently when engaged in a selected one of a plurality of defined orientations.

Some embodiments of orthodontic appliances according to the present disclosure may be adapted to prevent, or restrict, relative rotation or other relative movement of the assemblies when engaged, such as with coupling portions. Restricting relative movement may assure that, when the coupling portions are engaged, the forces exerted by the archwire on the corrective assembly are directed to the tooth in a selected, or predetermined, direction, such as may be selected by an orthodontist or otherwise consistent with orthodontic treatment, without being inadvertently misdirected, for example, by components of the orthodontic appliance that may have become misaligned.

Some embodiments of orthodontic appliances according to the present disclosure may include visual indicia to visually indicate if the coupling portions are misaligned, disengaged, or otherwise incorrectly engaged. Such visual indicia may assist a patient or an orthodontist in determining if a corrective assembly of an orthodontic appliance is incorrectly engaged or aligned with a corresponding support assembly. This determination may be useful during installation of the corrective assembly, and/or thereafter, such as when a patient receives a force that potentially may have decoupled the coupling portions of one or more orthodontic appliances in a patient's mouth. For example, the visual indicia may include a colored surface on a coupling portion and/or other part of the orthodontic appliance. Such a colored surface may be positioned to be occluded from view when the corrective assembly is properly engaged with the support assembly, such that a visible colored surface may alert a patient or an orthodontist that a corrective assembly should be re-engaged, or correctly aligned, with its corresponding support assembly.

Further, although a corrective assembly that disengages from a support assembly may be coupled to or otherwise engaged with the archwire, and thus, to some extent, restrained from movement, some embodiments of orthodontic appliances according to the present disclosure may include a tether device that is adapted to limit the movement of a disengaged corrective assembly. For example, such embodiments may include a tether device in the form of a hinge mechanism that connects the coupling portions of the corrective and support assemblies and thereby retains a linkage between the assemblies if the assemblies are disengaged. Such a tether device may in some configurations provide an alignment feature and/or restrict relative movement of engaged assemblies.

The coupling portions and other components of the aforementioned illustrative embodiments of orthodontic appliances according to the present disclosure may take any desired, or suitable, configuration, such as those included in some of the exemplary orthodontic appliances disclosed in further detail in the drawings and detailed description below.

During orthodontic treatment, adjustment of the corrective forces that are directed to a tooth by an orthodontic appliance according to the present disclosure may be affected, for example, by exchanging the corrective assembly of an orthodontic appliance with another corrective assembly that is configured to direct corrective forces differently. Thus, a set of orthodontic appliances according to the present disclosure may, but is not required to, include a plurality of support assemblies and a plurality of interchangeable corrective assemblies, the plurality of interchangeable corrective assemblies including at least a first corrective assembly and a second corrective assembly, such that the second corrective assembly is configured to direct corrective forces differently from the first corrective assembly. Such a set may enable the manner in which corrective forces are directed to a particular tooth to be adjusted without removal of the support assembly from the tooth, or replacement or reconfiguration of the archwire. Instead, a corrective assembly may be selected from a group, or plurality, of corrective assemblies that are configured to direct the corrective forces differently from each other, and which may be exchanged when adjustment is desired.

Embodiments of a self-release assembly for use with a corrective orthodontic bracket are also disclosed herein, for example to enable an orthodontist to retrofit a conventional set of orthodontic hardware, and even a previously installed set of orthodontic hardware, with a self-release assembly, or mechanism, according to the present disclosure.

Thus, some embodiments may provide an existing orthodontic bracket with a support assembly and an engagement assembly to accommodate the orthodontic bracket. The support assembly may further include a tooth engaging portion adapted to bond the support assembly to a tooth and a support portion extending from the tooth engaging portion, and the engagement assembly may further include a first coupling portion on the support portion, and a second coupling portion adapted to be attached to an orthodontic bracket. In such embodiments, the engagement assembly is configured to releasably engage the first and second coupling portions, and to disengage the first and second coupling portions responsive to a force exceeding a predetermined value applied to the orthodontic bracket.

Another configuration of a self-release assembly according to the present disclosure may be configured for use with an existing bracket by providing a corrective assembly (instead of a support assembly) and an engagement assembly to accommodate the orthodontic bracket. The corrective assembly may include a wire engaging portion adapted to receive archwire and a base portion extending from the wire engaging portion and generally away from the archwire. The engagement assembly may include a first coupling portion on the base portion, and a second coupling portion adapted to be attached to a corrective orthodontic bracket. The engagement assembly may be configured as described herein.

An illustrative, non-exclusive example of a multi-piece, reusable orthodontic appliance according to the present disclosure is schematically illustrated in FIG. 1 and generally indicated at 10. Appliance 10 is generally configured to be bonded to a tooth 12, such as via bonding media 14, and more specifically to receive or otherwise engage an archwire 16 and transmit corrective forces from the archwire to the tooth. In particular, appliance 10 includes a support assembly 20 and a corrective assembly 22. As explained in greater detail herein, support assembly 20 is adapted to be bonded or otherwise secured to a tooth, and corrective assembly 22 is adapted to receive the archwire and to direct corrective forces exerted by the archwire to the tooth. Furthermore, support assembly 20 and corrective assembly 22 are configured to be releasably attached, or engaged, together to collectively form orthodontic appliance 10. However, corrective assembly 22 is configured to disengage from support assembly 20 in response to a force applied to the corrective assembly.

The components and/or structural features of support assembly 20 and corrective assembly 22 may be configured as desired to enable repeated engagement and disengagement of the assemblies, without destruction or deterioration to any of the components of the appliance caused by engaging or disengaging the coupling portions. In particular, the first and second coupling portions may be configured to be reusable after being disengaged, for example by being fabricated to remain structurally intact upon engagement and disengagement. Thus, for example, an orthodontist may install several appliances 10 to the teeth of a patient, for orthodontic treatment, without having to replace components that become damaged due to disengagement during the period of the treatment. Instead, the orthodontist, or in some embodiments even the patient, may reengage any detached components, resuming treatment. Accordingly, the components, or assemblies, of orthodontic appliances according to the present disclosure are adapted to be repeatedly disengaged and reengaged without destructions of the components, or assemblies. For example, the corrective assemblies of an orthodontic appliance according to the present disclosure may be adapted to be disengaged from a corresponding support assembly that is coupled to a tooth in a patient's mouth. Should the corrective assembly be disengaged from the support assembly, such as described herein, neither the support assembly nor the corrective assembly is damaged or otherwise rendered unable to be used as part of an orthodontic appliance 10 according to the present disclosure. Accordingly, the assemblies may be reengaged, and thereby reused. However, it is not a requirement for an orthodontic appliance 10 to always have its support and corrective assemblies reengaged for reuse of both assemblies in all embodiments and at all times. For example, during orthodontic treatment, in some situations it may be desirable to intentionally disengage the support and corrective assemblies of an orthodontic appliance 10 according to the present disclosure and to reengage the support assembly, which is still coupled to a tooth, to a different corrective assembly. It is further within the scope of the present disclosure, though not required, that the disengaged corrective assembly may be reengaged with a different support assembly for further use. Therefore, orthodontic appliances 10 may be described as being "reusable" even though reuse is not required to all embodiments or in all applications.

Orthodontic appliances 10 according to the present disclosure have also been described as being "multi-piece" orthodontic appliances. As used herein, "multi-piece" refers to an orthodontic appliance that is a composite structure consisting of at least two components, namely, at least support assembly 20 and corrective assembly 22. Therefore, orthodontic appliances according to the present disclosure may include two components, three components, four components, or more. The support and corrective assemblies may be single-piece components, such as which include a monolithic body, or base portion. However, it is also within the scope of the present disclosure that the support and coupling assemblies themselves may be composite structures consisting of two or more separable subcomponents, or that the various components and structural features of each assembly may be integrally formed.

For example, and with continuing reference to FIG. 1, support assembly 20 includes a tooth engaging portion 30 that is adapted to be bonded to a tooth 12. The support assembly further includes a support portion 32 extending from the tooth engaging portion generally away from the tooth. As illustrated, the support portion includes a first coupling portion 34 that is adapted to be releasably coupled to, or engaged with, corrective assembly 22.

Figure 2:
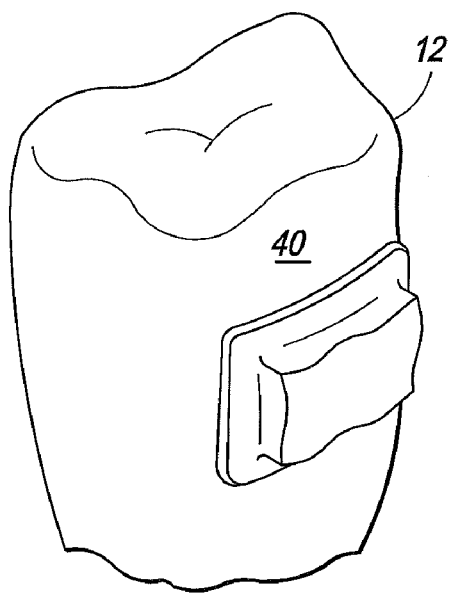
FIG. 2 is a fragmentary isometric view showing an exemplary tooth engaging portion of an orthodontic appliance bonded directly to a tooth surface.
Figure 3:
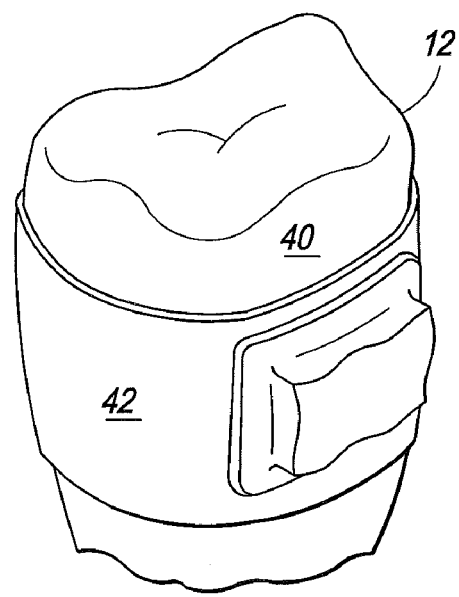
FIG. 3 is a fragmentary isometric view showing an exemplary tooth engaging portion of an orthodontic appliance bonded to a band that encircles a tooth.

Tooth engaging portion 30 may include a tooth-facing rear surface 36, which may be configured as desired for being bonded or otherwise secured to tooth 12, such as with bonding media 14. As used herein, the front surface, or region, of an assembly or component generally refers to the surface or region that is adapted to face away from the tooth to which the corresponding appliance 10 is coupled during use, while the rear surface, or region, of an assembly or component generally refers to the surface or region that is adapted to face the tooth to which the corresponding appliance 10 is coupled during use of the appliance. Direct contact between the tooth-facing rear surface of the tooth engaging portion is not required. Accordingly, the tooth engaging portion may additionally or alternatively be referred to as a tooth-facing portion 30, and/or a portion 30 that is adapted to be bonded to a tooth. For example, rear surface 36 may be adapted to be bonded with a bonding media, such as a suitable cement and/or other adhesive, either directly to a tooth surface 40 as shown in FIG. 2, or to a tooth band 42 that is secured around tooth 12, as shown in FIG. 3. As such, rear surface 36 may be generally planar or contoured, smooth or textured, and/or may include ribs or other structure configured to secure the tooth engaging portion 30 to the tooth to achieve a bond of any desired strength.

As illustrated in FIG. 1, support portion 32 extends from tooth engaging portion 30, generally away from tooth 12. First coupling portion 34 is situated on support portion 32, and as such may be integrally formed with support portion 32, or may be a separate structure that is coupled to the support portion, such as during fabrication, prior to installation of the appliance in a patient's mouth, or even during installation, by any appropriate means, such as which may include mechanical, magnetic, and/or other suitable types of linkages, adhesive bonding, and so forth.

Corrective assembly 22 includes a wire engaging portion 50 that is adapted to receive archwire 16, a base portion 52 extending from the wire engaging portion and generally away from the archwire, and a second coupling portion 54 on the base portion. The wire engaging portion of orthodontic appliance 10 may be configured as desired to receive or otherwise accommodate an archwire, and the configuration may assist direction of corrective forces to the tooth. Thus, although other methods of accommodating an archwire are possible, wire engaging portion 50 may include a front surface 56 with an archwire slot 58, into which the archwire may be seated. Wire engaging portion 50 may further include structure adapted to secure archwire 16 in place with respect to orthodontic appliance 10, such as suitable structure to retain the archwire within archwire slot 58.

Figures 4, 5:
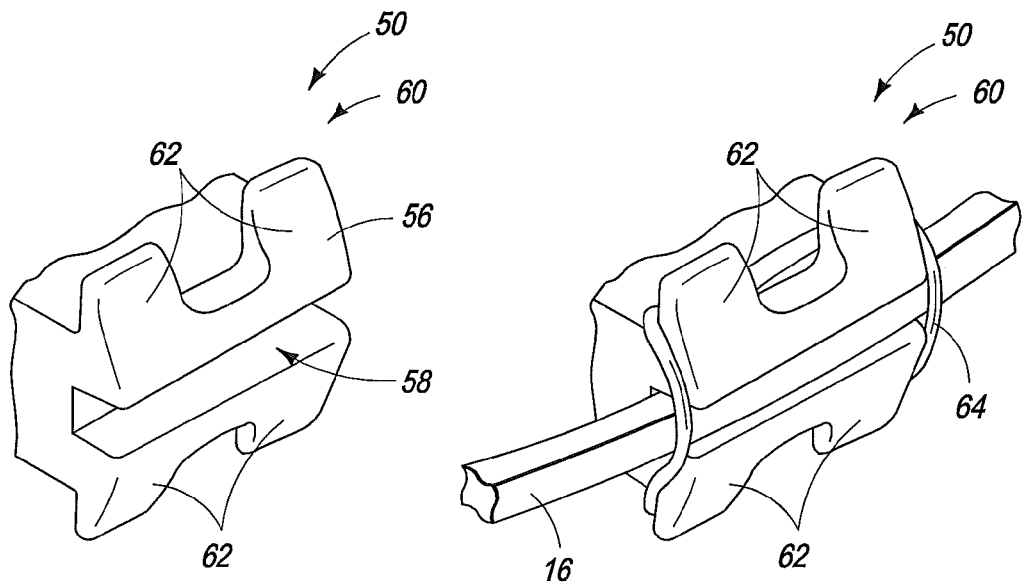
FIG. 4 is a fragmentary isometric view showing an exemplary ligating wire engaging portion of an orthodontic appliance, such as may be used with orthodontic appliances according to the present disclosure.
FIG. 5 is a fragmentary isometric view showing the ligating wire engaging portion of FIG. 4 engaging an archwire.

For example, wire engaging portions 50 according to the present disclosure may include structural features of, or similar to, a ligating orthodontic bracket. An example of such a wire engaging portion 50 is shown in FIGS. 4 and 5 and is indicated generally at 60. In FIG. 4, an exemplary ligating wire engaging portion 60 is shown to include a front surface, or region, 56 featuring an archwire slot 58 and tie wings 62 that are arranged adjacent to the archwire slot, such as the sets of tie wings shown in FIG. 4 on either side of the archwire slot. As seen in FIG. 5, tie wings 62 may be used in coordination with a ligature wire, elastic band, or other securing device 64 in order to secure archwire 16 in a desired position with respect to the ligating wire engaging portion.

Figures 6, 7:
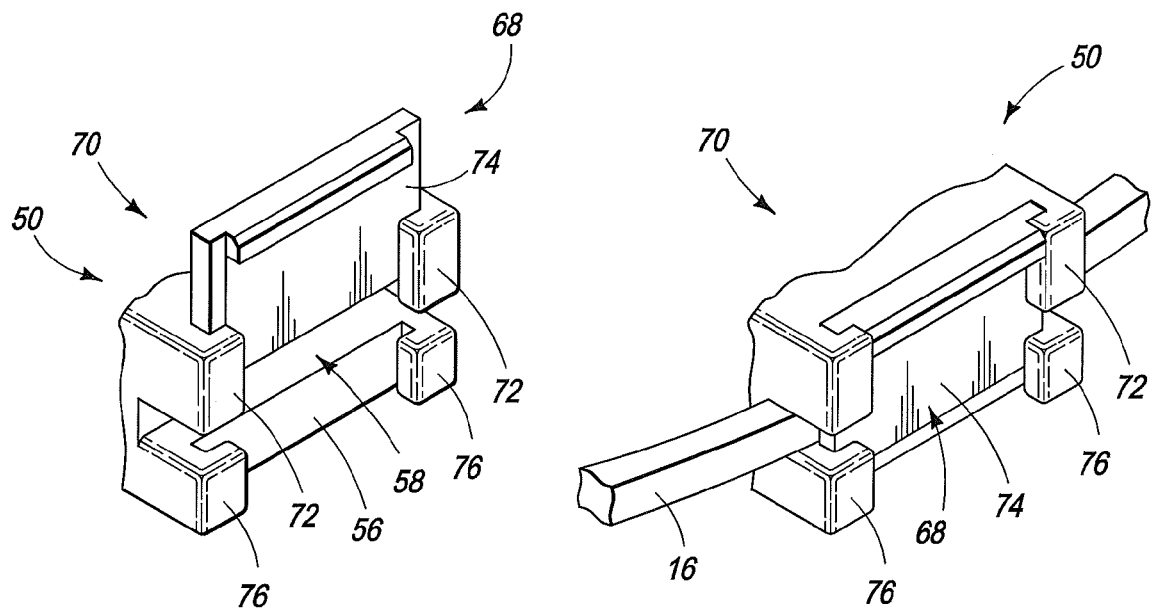
FIG. 6 is a fragmentary isometric view showing an exemplary self-ligating wire engaging portion of an orthodontic appliance, such as may be used with orthodontic appliances according to the present disclosure.
FIG. 7 is an isometric view showing the self-ligating wire engaging portion of FIG. 6 engaging an archwire.

It is also within the scope of the present disclosure that the wire engaging portion may include structural features of, or similar to, a self-ligating orthodontic bracket 68. For example, the wire engaging portion may include a releasable clamp, gate, clasp, or other suitable locking structure that is adapted to releasably secure an archwire within the archwire slot. An illustrative example of a self-ligating orthodontic bracket 68 with a self-ligating wire engaging portion is shown in FIGS. 6 and 7 and is generally indicated at 70. In FIG. 6, the exemplary self-ligating wire engaging portion 70 is shown to include a front surface 56 with an archwire slot 58 and a pair of support arms 72 disposed on one side of the archwire slot. Support arms 72 support a slidable locking member 74. As seen in FIG. 7, slidable locking member 74 may be moved to engage a pair of receiving arms 76 disposed on the opposite side of the archwire slot, to secure archwire 16 in place with respect to the self-ligating wire engaging portion. Slidable locking member 74 essentially allows the self-ligating wire engaging portion to retain the archwire without the use of ligatures that are adapted to secure the archwire within the archwire slot. Member 74 may be described as being selectively slid, or otherwise moved, between a first, or open, configuration in which the member is positioned to penult the archwire to be inserted into and removed from the archwire slot, and a second, or locked, configuration in which the member extends sufficiently across the archwire slot to prevent removal of the archwire through the slot. It is within the scope of the present disclosure that other locking structures may be used in self-ligating wire engaging portions 70 according to the present disclosure. As an illustrative example, some locking structures may be adapted to pivot between locked and unlocked configurations, in which the locking structures are respectively positioned to retain or release the archwire from the archwire slot of a wire engaging portion to which the locking structure is secured.

Illustrative, non-exclusive examples of ligating orthodontic brackets that disclose structures and/or components that may be used with ligating wire engaging portions 70 according the present disclosure are disclosed in U.S. Pat. Nos. 6,302,688, 6,582,226, 4,878,840, 3,772,787, 4,248,588, 4,492,573, 4,614,497, 4,698,017, 1,280,628, 1,821,171, and 3,435,527, the complete disclosures of which are hereby incorporated herein by reference for all purposes. Illustrative, non-exclusive examples of self-ligating orthodontic brackets that disclose structures and/or components that may be used with self-ligating wire engaging portions 70 according to the present disclosure are disclosed in U.S. Pat. Nos. 6,659,766, 6,655,957, 6,358,045, 6,193,508, 5,857,850, 5,711,666, 5,562,444, 5,322,435, 5,094,614, 4,559,012, 4,531,911, 4,492,573, 4,419,078, 4,371,337, 4,077,126, 4,144,642, 4,248,588, 4,698,017, 3,772,787, 4,786,242, 4,559,012, 4,561,844, 4,655,708, 4,077,126, 4,419,078, 4,634,661, 4,197,642, 4,712,999 and 4,171,568, the complete disclosures of which are hereby incorporated by reference herein for all purposes. Additional examples of orthodontic brackets that include features that may be incorporated into orthodontic appliances according to the present disclosure are disclosed in U.S. Pat. No. 6,632,088, the complete disclosure of which is hereby incorporated by reference for all purposes. The above-incorporated examples of conventional ligating and self-ligating brackets may also be utilized with embodiments of orthodontic appliances according to the present disclosure that include at least a support assembly that is adapted to be releasably coupled (directly or indirectly) to a conventional orthodontic bracket that includes a monolithic body portion and/or which is otherwise adapted to be utilized without an orthodontic appliance according to the present disclosure.

Figure 8:
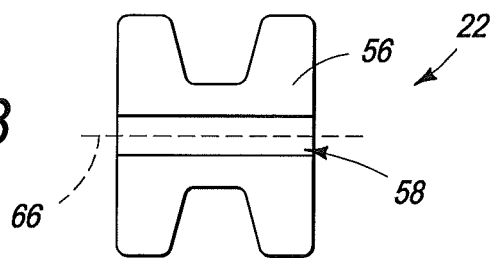
FIG. 8 is a front elevation view of an exemplary wire engaging portion of an orthodontic appliance, such as may be used with the corrective assemblies of orthodontic appliances according to the present disclosure.
Figure 9:
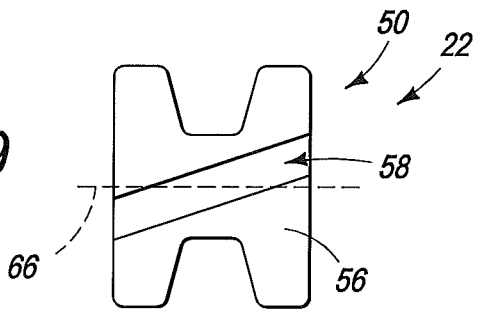
FIG. 9 is a front elevation view of another exemplary wire engaging portion of an orthodontic appliance, such as may be used with the corrective assemblies of orthodontic appliances according to the present disclosure.

Wire engaging portions 50 may be adapted to receive an archwire in any suitable orientation, for example by differing the orientation of archwire slot 58 with respect to the orthodontic appliance. For example, FIG. 8 shows a front view of an illustrative, non-exclusive example of a wire engaging portion 50 of an orthodontic appliance 10 that includes a front surface 56 with an archwire slot 58 that extends along a central, or lateral, axis 66 of the wire engaging portion. FIG. 9, however, shows an exemplary wire engaging portion 50 with an archwire slot 58 oriented at an inclined, or rotationally offset, angle with respect to central axis 66.

Figure 10:
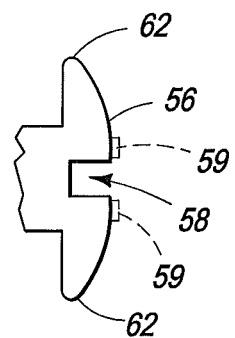
FIG. 10 is a fragmentary side elevation view of another exemplary wire engaging portion of an orthodontic appliance, such as may be used with the corrective assemblies of orthodontic appliances according to the present disclosure.
Figure 11:
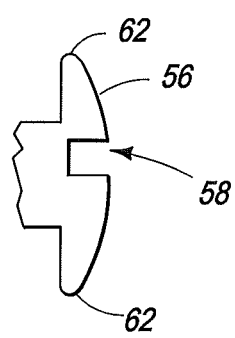
FIG. 11 is a fragmentary side elevation view of another exemplary wire engaging portion of an orthodontic appliance, such as may be used with the corrective assemblies of orthodontic appliances according to the present disclosure.
Figure 12:
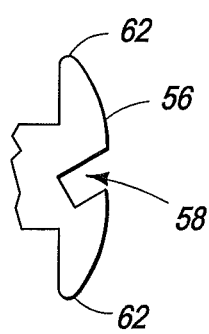
FIG. 12 is a fragmentary side elevation view of another exemplary wire engaging portion of an orthodontic appliance, such as may be used with the corrective assemblies of orthodontic appliances according to the present disclosure.

FIG. 10 shows a side view of the wire engaging portion of FIG. 8, in which the archwire slot 58 is shown to be disposed substantially central with respect to tie wings 62 and perpendicular with respect to front surface 56. FIG. 11 shows an exemplary wire engaging portion with an archwire slot offset from the center of the tie wings, and FIG. 12 shows an exemplary wire engaging portion with an archwire slot disposed at an angle with respect to an orientation perpendicular to the front surface.

Other orientations of archwire slot 58 are possible without departing from the scope of the present disclosure. For example, the archwire slot may be sized to receive an archwire completely within the slot (i.e., completely internal of the front surface of the wire engaging portion, or only partially within the slot, in which case a portion of the archwire will project from the archwire slot and/or front surface of the wire engaging portion. As another example, the depth of the archwire slot may change along the length of the slot instead of being constant along the length of the slot. Also, the archwire slot is shown in FIGS. 8-12 as a generally straight passage, or path, along the front surface of the wire engaging portion, but the slot may describe, or form, a curved passage, or path, in some embodiments. Further, the archwire slot in FIGS. 8-12 is shown to accommodate an archwire with a rectangular cross-section, but the shape of the archwire slot may vary without departing from the scope of the present disclosure, such as to accommodate an archwire of any suitable cross-sectional configuration. For example, the archwire and/or archwire slot may, but are not required to, have at least one of circular, semi-circular, rectangular, elliptical, irregular, symmetrical, monolithic, braided, uniform, and/or non-uniform cross-sectional configurations.

It is within the scope of the present disclosure that orthodontic appliance 10 may include a wire engaging portion 50 that is configured to engage an archwire by means other than an archwire slot, for example by including one or more fastening devices configured to secure or otherwise engage an archwire directly to a surface of the wire engaging portion. For example, a wire engaging portion of a corrective assembly according to the present disclosure may include, additionally or alternatively, one or more ribs or other projections that extend from the front surface to define an archwire receiving region. This region may extend completely external the front surface of the wire engaging portion, or may be used in cooperation with an archwire receiving slot. Such a projecting region is schematically illustrated in FIG. 10 at 59.

Returning to FIG. 1, base portion 52 of corrective assembly 22 is shown extending from wire engaging portion 50, generally away from archwire 16. Second coupling portion 54 is situated on base portion 52, and, like first coupling portion 34, may be integrally formed with base portion 52, or may be a separate structure coupled to the base portion, such as during fabrication, prior to installation, or during installation, by any appropriate means including mechanical, magnetic, and/or other types of linkages, adhesive bonding, and so forth.

The first and second coupling assemblies may be collectively referred to herein as an engagement assembly 55, which is adapted to releasably engage the support and corrective assemblies. Once so engaged, the engagement assembly may be adapted to release the corrective assembly from the support assembly responsive to a force applied to the corrective assembly. As discussed in more detail herein, the engagement assembly of orthodontic appliances according to the present disclosure is preferably coupled together by a weaker bond, or weaker attachment mechanism, than the bond or mechanism that couples the support assembly to a tooth. Therefore, the applied force will tend to disengage the corrective assembly from the support assembly, by disengaging the engagement assembly, rather than removing the entire appliance from a patient's tooth. As indicated above, it is within the scope of the present disclosure that the corrective assembly is adhesively bonded to the support assembly by a suitable bonding agent, or media. In such a configuration, the bonding agent preferably establishes a weaker bond between the corrective and structural assemblies than the bonding media that secures the corrective assembly to a tooth or tooth-encircling band.

Such a force may be corrective in nature, referring to a force administered in the course of orthodontic treatment, or non-corrective, referring to forces applied outside orthodontic treatment. Illustrative examples of non-corrective forces include, but are not limited to, forces that are applied during such daily activities as chewing food, brushing teeth, or biting upon a hard object. Such forces are usually applied in an occlusal direction, or generally parallel to the plane of the tooth surface. When such forces encounter an orthodontic bracket of monolithic body construction, such as a conventional ligating or self-ligating bracket, the bracket is usually urged to one side in an occlusal direction, effectively "peeling" the bracket from its position on a tooth. Thus, such brackets usually debond from the tooth surface upon receiving a "peel" force or other force of greater magnitude than the strength of the bond between the tooth and such a bracket. In some cases, instead of debonding, such brackets may fracture, destroying the bracket, or transmit the non-corrective force to the tooth, damaging the tooth surface or other part of the tooth. Non-corrective forces may also include those resulting from a sudden blow or other impact, which may be applied in virtually any direction. Also, during orthodontic treatment, a corrective force may result in damage to the tooth and/or to the bracket, for example if such a force is incorrectly administered by an orthodontist, or inadvertently misdirected due to orthodontic hardware that has become misaligned or incorrectly oriented. The various forces to which an orthodontic appliance is subjected may vary due to such factors as the relative position of the tooth to which an appliance is attached in the dental arch, the direction and/or strength of the corrective forces exerted on the tooth by the archwire, and so forth.

Thus, orthodontic brackets of monolithic body construction may cause damage to a tooth during debondment. Moreover, even if such a monolithic bracket debonds from a tooth without damage to either the tooth or to the bracket, the tooth surface may be abraded or otherwise damaged by repeated debonding and reattachment of the bracket. Similarly, a conventional orthodontic bracket will require cleaning and preparation of at least one, or both, of the bracket and tooth surface prior to reinstallation of the bracket. Reinstallation also requires careful positioning of the bracket to reinstall the bracket in the correct location on the tooth and/or relative to other orthodontic brackets.

An orthodontic appliance 10 with an engagement assembly 55 according to the present disclosure may, but is not required to, protect against inadvertent damage to a tooth such as may be caused by such forces. Different configurations of engagement assembly 55 may be adapted to release upon application of a force of a predetermined value, such as a value less than a force sufficient to debond the support assembly from the tooth, and/or upon application of a force applied in a predetermined direction. A force greater than a predetermined value that is applied to a corrective assembly engaged with a support assembly by an engagement device may simply dislodge the corrective assembly and leave the support assembly attached to the tooth, rather than debond the entire orthodontic appliance from the tooth. Re-engagement of detached corrective assemblies does not require contact with the tooth surface. Moreover, a releasable configuration may reduce tooth damage by reducing or completely preventing transfer of mechanical force to the tooth or gums, which may be the case with a conventional bracket that is either dislodged as a unit or which does not dislodge and thereby transmits the applied force to the patient's tooth.

Orthodontic appliances 10 according to the present disclosure that include an engagement assembly 55 configured to releasably engage a corrective assembly with a support assembly may also, but are not required to, reduce interruptions in orthodontic treatment. For example, an orthodontic bracket of monolithic body construction may accidentally debond from a tooth in response to an applied force such as those described above, necessitating a session of orthodontic maintenance in which the bracket is rebonded to the tooth in order to resume orthodontic treatment. An engagement assembly that allows a corrective assembly to disengage a support assembly responsive to a force may be configured to be readily re-engaged, which may allow for reduced chair time for an orthodontic patient.

Although not required to all embodiments, some engagement assemblies 55 according to the present disclosure may be configured to be sufficiently simple to re-engage that a patient may be able to re-attach disengaged assemblies without having to schedule an orthodontic appointment. Some embodiments may optionally include an alignment feature, for example to assist and/or assure proper engagement of a corrective assembly with a support assembly, either in initial installation or when reattaching a disengaged corrective assembly. More specifically, some coupling portions may be configured to engage only when urged together in a predetermined orientation. For example, in some embodiments, a first coupling portion may include a shaped male part adapted to fit within or otherwise engage a correspondingly shaped female part on a second coupling portion.

Moreover, some embodiments of engagement assemblies may include a feature to restrict or prevent some relative movement of the engaged coupling portions and/or the corrective and support assemblies, while permitting relative movement of the coupling portions and/or assemblies in another predetermined direction or manner. Such controlled movement may assure that forces exerted by the archwire on the orthodontic appliance are not misdirected due to improper alignment of the components of the appliance, while simultaneously allowing the coupling portions to disengage responsive to a non-corrective force applied to the appliance.

For example, once properly aligned and engaged, translational movement in an occlusal direction may be prevented, with translational movement in a labial direction (generally perpendicular to the tooth surface) permitted, with first and second coupling portions adapted to fit together in a snap fit relationship. In other words, such a snap fit relationship may allow the engaged assemblies to resist relative sideways, or lateral, movement, and instead direct such forces to disengage the snap fit in a direction generally perpendicular to the tooth. As another example, relative rotational movement may be prevented with correspondingly shaped male and female parts on the coupling portions. The predetermined direction and/or manner of permitted movement of the component parts of the appliance may relate to the nature of the forces that may be exerted on an orthodontic appliance, as mentioned above. In other words, some embodiments of appliances 10 according to the present disclosure may be configured to disengage the coupling portions in one or more predetermined directions while resisting forces received from other directions, and/or may redirect such received forces in order to disengage the coupling portions rather than allow such forces to be transmitted to the tooth.

As such, engagement assembly 55 of an orthodontic appliance 10 according to the present disclosure, or more specifically first coupling portion 34 and/or second coupling portion 54, may take any appropriate form, and may include any manner of components including mechanical linkages, magnetic linkages, adhesive linkages, and so forth, that are collectively configured to establish a connection or other engagement of the corrective assembly with the support assembly such that the engagement assembly will release responsive to a force exceeding a predetermined value applied to the corrective assembly. Some embodiments may, but are not required to, include combinations of such components. For example, some embodiments that include coupling portions that are adapted to fit together in a snap fit relationship may also include a magnetic linkage, such as a magnetically attractive part on one of the coupling portions and a magnetically attracted part on the other coupling portion.

In some embodiments, the engagement assembly of an orthodontic appliance 10 according to the present disclosure may, but is not required to, include visual indicia to visually indicate if the coupling portions are disengaged. Such visual indicia may assist a patient or an orthodontist to determine if a corrective assembly of an orthodontic appliance has become inadvertently disengaged from the corresponding support assemblies and/or is not properly positioned or aligned with a corresponding support assembly. For example, the visual indicia may include a colored, or otherwise visually contrasting or distinct, surface on a coupling portion or another suitable portion of the orthodontic appliance, with this portion being adapted to be occluded from view when the corrective assembly is properly engaged with the support assembly. Therefore, if the visual indicia is able to be seen when the orthodontic appliance is installed in a patient's mouth, then this indicates that the corrective assembly is not properly engaged or otherwise positioned relative to the corresponding support assembly. Because the visual indicia is designed to not be visible when the corrective assembly is properly coupled to a corresponding support assembly, the visual indicia may be selected to be very colorful or otherwise visually distinct from at least the front and/or side surfaces of the corrective assembly and/or a patient's teeth.

Figure 13:
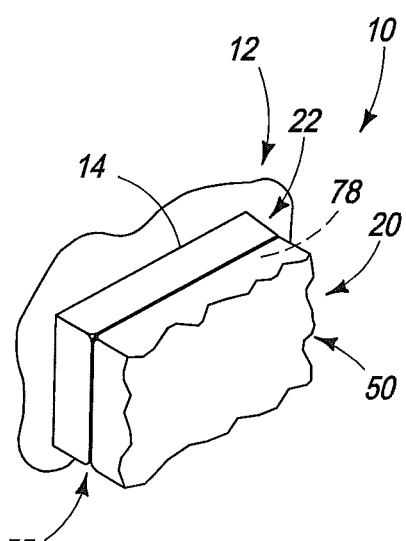
FIG. 13 is a schematic perspective view of an orthodontic appliance according to the present disclosure that includes visual indicia adapted to visually indicate when a corrective assembly of the appliance is disengaged or otherwise not properly positioned relative to the support assembly.
Figure 14:
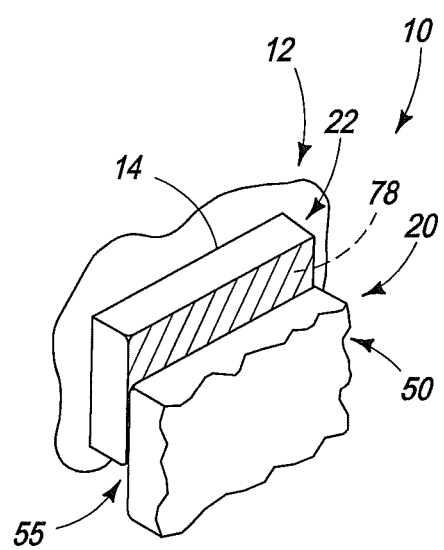
FIG. 14 is a schematic perspective view of the orthodontic appliance of FIG. 13 with the corrective assembly displaced from the position shown in FIG. 13, thereby exposing visual indicia.

In FIG. 13, a schematic example of an orthodontic appliance 10 according to the present disclosure is shown that includes a support assembly 20 and a corrective assembly 22 that is releasably coupled to the support assembly by an engagement assembly 55. Assemblies 20 and 22, and engagement assembly 55 may have any suitable configuration and structure, such as disclosed, illustrated and/or incorporated herein. As indicated in dashed lines in FIG. 13, at least a portion of the support assembly and/or engagement assembly that faces away from the tooth 12 to which the appliance is coupled includes visual indicia 78 that is covered or otherwise occluded from view by the corrective assembly. FIG. 14 schematically illustrates the appliance of FIG. 13, with the corrective assembly displaced from its position shown in FIG. 13, thereby exposing visual indicia 78. In the illustrated schematic example, the corrective assembly has been translated laterally and vertically relative to the properly installed position shown in FIG. 13. In some embodiments, the corrective assembly may be restricted to one or more of lateral displacement, vertical displacement, and/or rotational displacement.

Also, although a corrective assembly that has become disengaged from a support assembly may still be engaged with the archwire and thus prevented from completely unrestrained movement, it is also possible for some forces that cause disengagement of the corrective assembly from the corresponding support assembly to permit complete removal of the corrective assembly. It is within the scope of the present disclosure that an orthodontic appliance 10 according to the present disclosure may, but is not required to, include a tether device that is adapted to couple the corrective assembly with the support assembly even when the assemblies are disengaged from each other. Such a tether device may be described as providing a physical linkage between the corrective assembly and the support assembly. This linkage may simply interconnect the assemblies, such as in the form of a flexible linkage that extends between the assemblies. In some embodiments, the tether device may be adapted to further limit movement of a disengaged corrective assembly and/or function as a movement restraining device in case the corrective assembly disengages the archwire. Such a tether device may take any desired form, such as a hinge mechanism that connects the coupling portions of the corrective and support assemblies. A hinge may additionally provide a simple mechanical alignment feature. In FIG. 1, a schematic representation of a tether device is indicated in dashed lines at 80 and is shown interconnecting the corrective and support assemblies of appliance 10.

One illustrative, non-exclusive method of orthodontic treatment suitable for use with an orthodontic appliance 10 according to the present disclosure may include bonding the tooth engaging portion of a support assembly to a tooth or a band that encircles a tooth, selecting one of a plurality of corrective assemblies configured to direct corrective forces to a tooth in a desired manner, engaging the first coupling portion of the support assembly with the second coupling portion on the selected corrective assembly, and then engaging the corrective assembly with an archwire. During orthodontic treatment, the corrective forces may be adjusted by disengaging the archwire, disengaging the first and second coupling portions, selecting another corrective assembly configured to direct corrective forces differently from the previously engaged corrective assembly, engaging the first coupling portion of the support assembly with the second coupling portion on the new corrective assembly, and then engaging the new corrective assembly with the archwire.

Several exemplary, non-exclusive embodiments of orthodontic appliances 10 according to the present disclosure are disclosed below in connection with FIGS. 15-45. The exemplary embodiments differ from each other primarily in terms of the different forms of coupling portions employed to releasably engage the corrective assembly with a support assembly. Alternative configurations and/or variants of several of the embodiments are also presented, such as to illustrate variations of structural components and arrangement of such components. The various embodiments, configurations, and methods disclosed in the paragraphs below are exemplary and should not be considered in a limiting sense, but merely for illustrative purposes of one or more of the aspects of the subject matter described herein. Numerous variations are possible and considered to be within the scope of this disclosure.

In FIGS. 15-45, the appliances are still somewhat schematically illustrated and may provide additional examples of some of the previously discussed and/or illustrated components, or sub-components, that may be incorporated into an orthodontic appliance within the scope of the present disclosure. The corrective assemblies in FIGS. 15-45 are illustrated in somewhat simplified form as including a ligating form of wire-engaging portion. As discussed, these corrective assemblies may alternatively take the form of a self-ligating wire engaging portion and/or any other wire engaging portion that is described, illustrated, and/or incorporated herein or otherwise consistent with the present disclosure. Similarly, any of the following examples or orthodontic appliances may be utilized with a visual indicia 78 and/or tether 80, may have any suitable relative size and shape, and may be installed directly to a tooth or to a band that surrounds a tooth. It is within the scope of the present disclosure that components, subcomponents, and variants of the subsequently described FIGS. 15-45 may be used with other orthodontic appliances within the scope of the present disclosure, such as in others of FIGS. 15-45, in FIGS. 1-14, and/or otherwise described and/or incorporated herein. In FIGS. 15-45, various components and subcomponents of the corrective and/or support assemblies are indicated with reference numerals that are similar to the above-described reference numerals but which are incremented in at least units of 100 to provide different reference numerals between different illustrative embodiments even though some or all of the embodiments may include the same components, sub-components and/or variants. As an example, reference numerals 10, 110, 210, 310, etc. all indicate orthodontic appliances according to the present disclosure, reference numerals 20, 120, 220, 320, etc. all indicate support assemblies, while reference numerals 22, 122, 222, 322, etc. all indicate corrective assemblies. For the purpose of brevity, each introduction of a new reference numeral for a previously described component or subcomponent will not include another discussion of the fact that the component or subcomponent may include any suitable structure, such as which is described, illustrated and/or incorporated herein.

In FIG. 15, another illustrative example of an orthodontic device 10 according to the present disclosure is shown and generally indicated at 110. Orthodontic appliance 110 is shown to include a support assembly 120 and a corrective assembly 122. Support assembly 120 further includes a tooth engaging portion (which as discussed may also be referred to as a tooth-facing portion) 124 consisting of a tooth-facing rear surface 126, a support portion 128 in the form of a contoured pedestal-like structure, and a first coupling portion 130 disposed on the support portion. Corrective assembly 122 further includes a ligating-style wire engaging portion 132 similar to that shown in FIGS. 4-5, which includes an archwire slot 134 and two pairs of tie wings 136 disposed to either side of the archwire slot. Corrective assembly 122 also includes a base portion 138 extending away from the wire engaging portion, and a second coupling portion 140 disposed on the base portion.

First coupling portion 130 is shown to include a male part 142 protruding from a front surface 144 of the support assembly, and second coupling portion 140 is shown to include a corresponding female part 146 disposed on a rear surface 148 of the corrective assembly. As shown in greater detail in FIGS. 16 and 17, male part 142 has a slightly rounded annular edge and a generally circular cross-section, the diameter of which slightly increases as male part 142 extends from surface 144. Female part 146 is correspondingly shaped, allowing first and second coupling portions to be releasably engaged in a snap fit arrangement. In such an embodiment, the male and female parts should be constructed to permit repeated engagement and disengagement of the parts without destruction of the parts. In FIG. 16, male portion 142 is shown including optional relieved regions 143 that may be included to assist in the male portion flexing or otherwise deflecting to permit snap-fit engagement with the female portion. FIG. 18 shows orthodontic appliance 110 with corrective assembly 122 engaged with support assembly 120 by means of the first and second coupling portions, which may be described as forming an engagement assembly 155. When appliance 110 includes visual indicia that indicates when the corrective assembly is not properly engaged or otherwise positioned with respect to the support assembly, the visual indicia may be present on front surface 144 of the support assembly, such as indicated in dashed lines at 156 in FIG. 16. The cross-sectional and perimeter shapes of the illustrative examples of male and female parts 142 and 146 are intended to provide illustrative, non-exclusive examples, with it being within the scope of the present disclosure that any suitable shape and configuration may be used.

Figure 19:
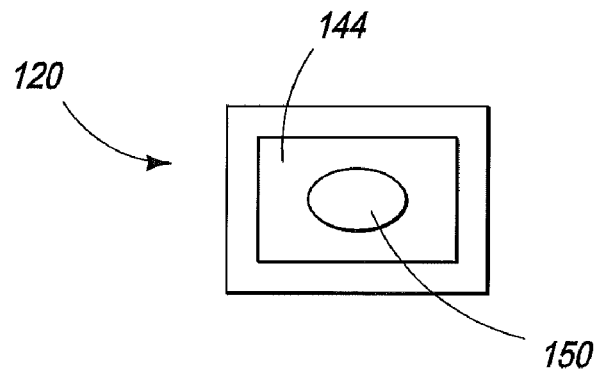
FIG. 19 is a front elevation view of another suitable support assembly for orthodontic appliances according to the present disclosure.
Figure 20:
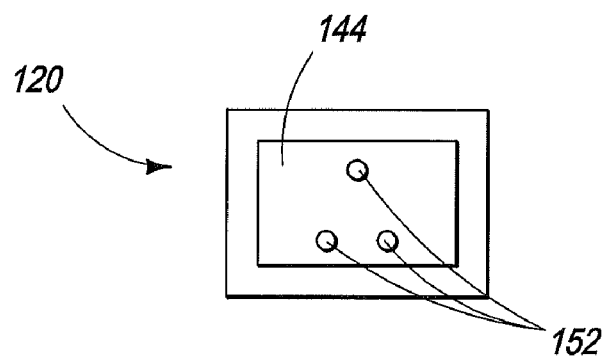
FIG. 20 is a front elevation view of another suitable support assembly for orthodontic appliances according to the present disclosure.
Figure 21:
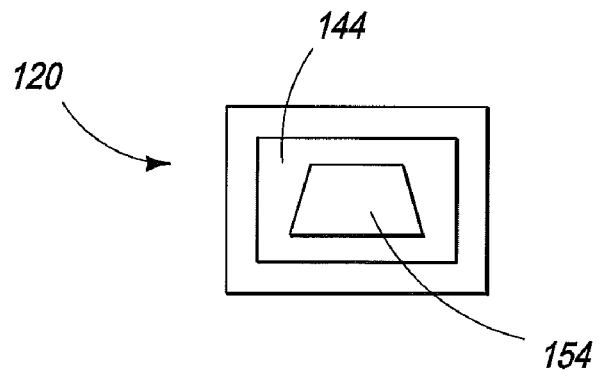
FIG. 21 is a front elevation view of another suitable support assembly for orthodontic appliances according to the present disclosure.

Orthodontic appliances according to the present disclosure may be adapted to enable or prevent relative rotation of the corrective assembly relative to the support assembly when the corrective assembly is properly engaged with the support assembly. For example, in the illustrative embodiment shown in FIGS. 15-18, the coupling portions were adapted to couple the corrective and support assemblies together while also permitting relative rotation of the corrective assembly with the support assembly. Orthodontic appliances according to the present disclosure may alternatively be configured to restrict relative rotation of the corrective and support assemblies, such as with the coupling portions. For example, relative rotation may be restricted, or even prevented, with corresponding male and female portions of appropriate shapes. As an illustrative example, FIG. 19 shows a front view of a configuration of support assembly 120, which includes a front surface 144 from which an elliptically-shaped male part 150 protrudes. FIGS. 20 and 21 show additional examples of rotation-restricting configurations of support assemblies. In FIG. 20, three male parts 152 protrude from surface 144, and the configuration in FIG. 21 is shown to include a quadrilaterally shaped male part 154. In each of these configurations, a correspondingly shaped female part engaged with the illustrated coupling portions would prevent rotation of the corrective assembly relative to the support assembly.

A shaped male part (and correspondingly shaped female part) may serve as an alignment feature, such as to assist a patient or an orthodontist in re-engaging a corrective assembly that has disengaged a support assembly.

For example, the elliptically shaped male part shown in FIG. 19 has two-fold rotational symmetry, allowing it to engage a correspondingly shaped female part in either of two orientations, each 180° apart. If a corrective assembly that also has two-fold rotational symmetry includes a correspondingly shaped female part, then either orientation would be appropriate for correct engagement with the support assembly. In other words, the elliptical shape of the male and female parts may ensure correct orientation by permitting engagement only when the two assemblies are urged together in one of the two orientations.

Alternatively, a corrective assembly with a correspondingly shaped elliptical female part may be configured to direct corrective forces differently in one orientation with respect to the other, such as with an inclined archwire slot or some other asymmetrical feature. Such a corrective assembly may thus include directional indicia (not shown) to visually distinguish the two orientations.

The alternative configurations shown in FIG. 20, featuring three male parts arranged to form an isosceles triangle (or other non-equilateral triangle), and in FIG. 21, featuring a quadrilateral with two non-parallel opposing sides, have no rotational symmetry, which may restrict engagement with a coupling portion with correspondingly shaped female parts to only one orientation.

Optionally, although not indicated in FIGS. 15-21, the surfaces 144, 148 of the support and corrective assemblies may be configured to be flush or closely adjacent when coupling portions 130, 140 are engaged, and as such may be correspondingly textured, contoured, or otherwise formed to mate or interlock in a matter that restricts translational and/or rotational movement of the corrective assembly relative to the support assembly.

Also as mentioned above, the orthodontic appliance may include visual indicia to visually indicate if the coupling portions are disengaged, or are misaligned or otherwise incorrectly engaged, such as to assist a patient or an orthodontist in determining if a corrective assembly of an orthodontic appliance is incorrectly engaged or aligned with the corresponding support assembly, or in correctly aligning the corrective assembly with the support assembly for engagement.

Figure 22:
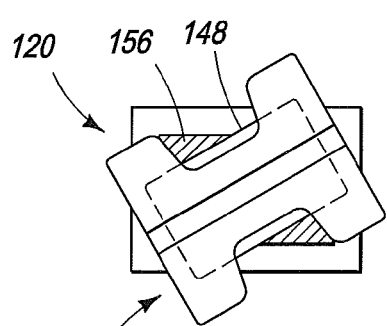
FIG. 22 is a front view of the orthodontic appliance of FIG. 18, showing the support assembly engaged with the corrective assembly in an incorrect orientation.
Figure 23:
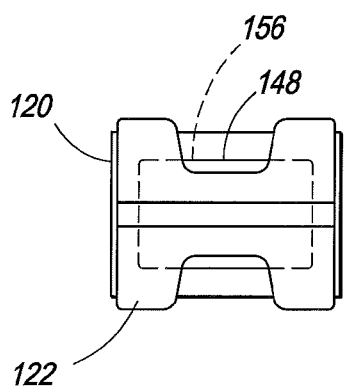
FIG. 23 is a front view of the orthodontic appliance of FIG. 22, showing the support assembly engaged with a corrective assembly in a correct orientation.

For example, the configuration of support assembly 120 in FIG. 16 is indicated in dashed lines to include visual indicia 156, as a color on surface 144. As shown in greater detail in FIGS. 22 and 23, colored surface or other visual indicia 156 may indicate if corrective assembly 122 is disengaged from, or misaligned with, support assembly 120. FIGS. 22 and 23 represent front views of this configuration, as might be seen by an orthodontist or a patient upon visual inspection of the patient's orthodontic hardware. In the view shown in FIG. 22, the appearance of colored surface 144 may indicate that corrective assembly 122 is not correctly engaged with support assembly 120. Thus, the patient or orthodontist may rotate corrective assembly 122 until surface 148 on the corrective assembly occludes colored surface 144, indicating correct alignment of the assemblies. If necessary, the corrective assembly may then be urged against the support assembly to engage the coupling portions in the correct alignment.

Figure 24:
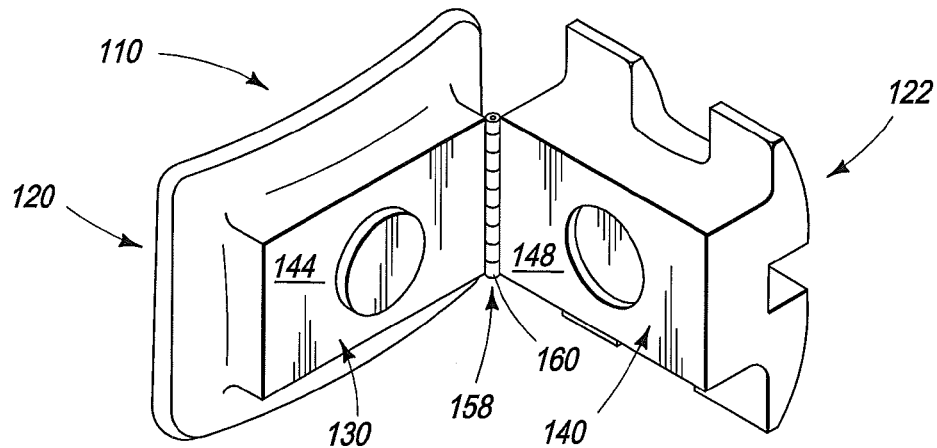
FIG. 24 is an isometric view of another orthodontic appliance according to the present disclosure.

Another optional configuration of orthodontic appliance 110 is shown in FIG. 24 and includes a tether device 158. Tether device 158 is illustrated to be in the form of a mechanical hinge 160 disposed at corresponding edges of surfaces 144, 148 of coupling portions 130, 140. Tether device 158 thus limits the movement of corrective assembly 122 from support assembly 120 if the former disengages the latter, even if the disengaged corrective assembly is still coupled to an archwire (not shown in this view). In this configuration, hinge 160 may also function as an alignment feature, providing correct orientation of the assemblies as they are urged together to engage the coupling portions. As such, hinge 160 may further include a spring member (not shown) or be otherwise biased toward a closed, open, or intermediate position. Further, although not shown in this view, surface 144 may be colored to visually indicate that hinge 160 has "sprung" open and that corrective assembly 122 has disengaged support assembly 120. Moreover, hinge 160 may be offset in some manner to enhance the visibility of such a colored surface upon disengagement of the corrective assembly. It is within the scope of the present disclosure that the tether device, when present, may couple any of the edges or other portions of the support and corrective assemblies together, with the lateral edges shown in FIG. 24 merely providing an illustrative configuration. For example, the particular tooth that an orthodontic appliance will be coupled to may influence whether a tether is used and/or which edges or other portions of the assemblies should be linked by the tether.

Figure 25:
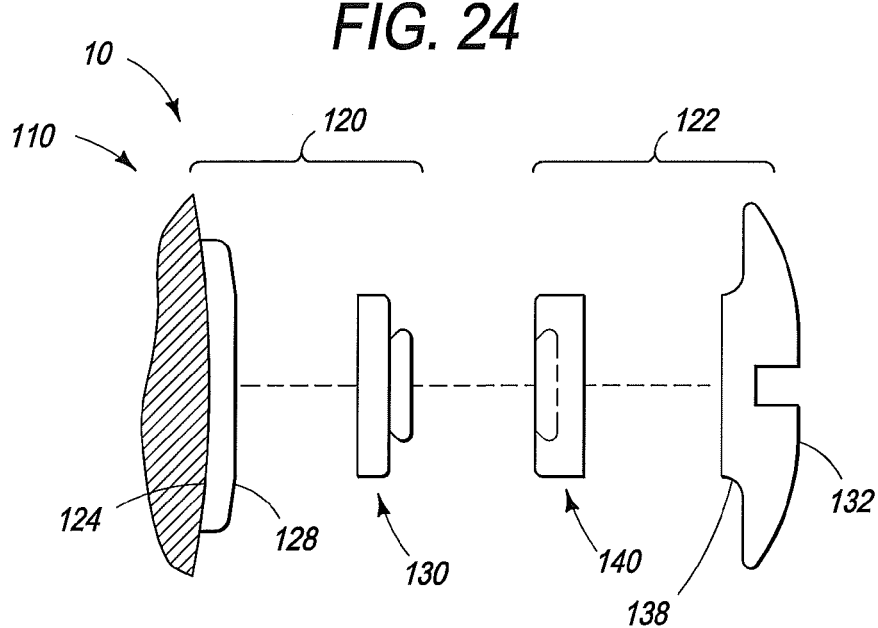
FIG. 25 is an exploded side view of another orthodontic appliance according to the present disclosure.

The various configurations of orthodontic appliance 110 are illustrated in FIGS. 14-24 to include support assembly 120 and corrective assembly 122, both of which are shown to be integrally formed structures. However, as mentioned above, one or both assemblies may instead be composite structures formed of two or more components. For example, FIG. 25 shows an exploded view of an embodiment of orthodontic appliance 110 in which support assembly 120 is shown to consist of separate parts including support portion 128 (shown to include tooth engaging portion 124) and first coupling portion 130. Somewhat similarly, corrective assembly 122 is shown to consist of separate parts including base portion 138 (shown to include wire engaging portion 132) and second coupling portion 140. Still other configurations may include other arrangements of integral and composite parts. In such a configuration, the various parts may be attached together by any suitable means, including by threaded connectors and/or other mechanical linkages, magnetic linkages, adhesive linkages, and so forth, as desired.

Also, the configurations shown in FIGS. 15-24 are all shown to include one or more male parts on the supportive assembly, with corresponding female parts on the corrective assembly. However, other configurations may be reversed with respect to this arrangement, for example with the male part(s) on the corrective assembly and corresponding female part(s) on the support assembly. Still other configurations may include both male and female parts on each assembly, arranged to engage when the assemblies are urged together.

Figure 26:
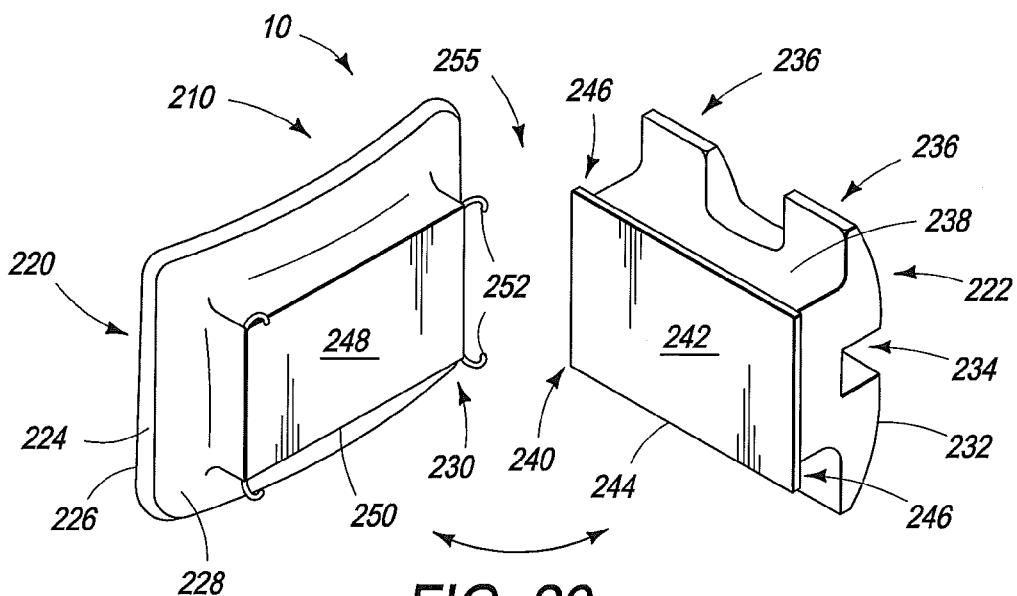
FIG. 26 is an exploded isometric view of another multi-piece, reusable orthodontic appliance according to the present disclosure.
Figure 27:
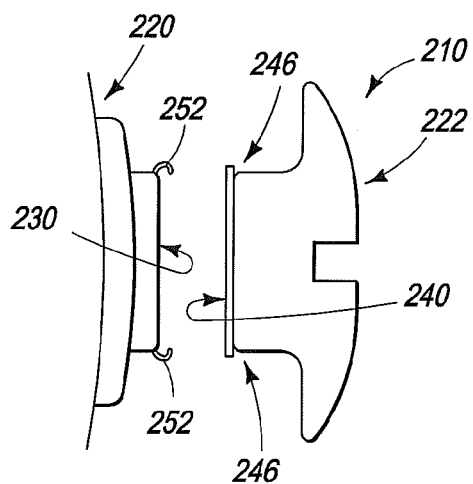
FIG. 27 is an exploded side elevation view of the orthodontic appliance of FIG. 26.
Figure 28:
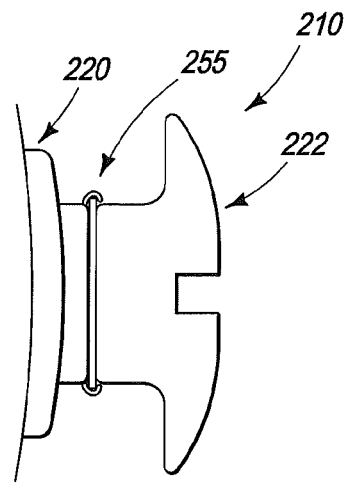
FIG. 28 is an assembled side elevation view of the orthodontic appliance of FIG. 26, with the support assembly engaged with the corrective assembly.

Another illustrative example of an orthodontic appliance 10 according to the present disclosure is illustrated in FIGS. 26-28. In FIG. 26, orthodontic appliance 210 is shown to include a support assembly 220 and a corrective assembly 222. Support assembly 220 further includes a tooth engaging (or tooth-facing) portion 224 consisting of a tooth-facing rear surface 226, a support portion 228 in the form of a contoured pedestal-like structure, and a first coupling portion 230 disposed on the support portion. Corrective assembly 222 further includes a ligating-style wire engaging portion 232 similar to that shown in FIGS. 4-5, which includes an archwire slot 234 and two pairs of tie wings 236 disposed to either side of the archwire slot. Corrective assembly 222 also includes a base portion 238 extending away from the wire engaging portion, and a second coupling portion 240 disposed on the base portion.

Second coupling portion 240 is shown to include a front surface 242 described by a rectangular peripheral edge 244. As also shown in FIG. 27, surface 242 forms a plane defining a surface area greater than that of base portion 238. In other words, the peripheral edge of the illustrative example extends past base portion 238 to form ledge portions 246.

As such, first coupling portion 230 is shown to include structural members that are adapted to engage the ledge portions 246 in a clip or clasp arrangement. In other words, the engagement assembly 255 formed by first and second coupling portions 230 and 240 includes a plurality of clasps or resilient barbs, or fingers, that are adapted to extend at least partially around a ledge portion of the corrective assembly to engage the corrective assembly with the support assembly. For example, first coupling portion 230 is shown in FIG. 26 to include a surface 248 also described by a rectangular peripheral edge 250, at the corners of which are disposed several inwardly curved resilient fingers 252. It is within the scope of the present disclosure that the number and/or position of the fingers, or other resilient retentive members, and/or the ledge and/or the perimeter shape of the assemblies may vary from the illustrative examples shown in FIG. 26.

As illustrated in FIG. 27, resilient fingers 252 of first coupling portion 230 are positioned and shaped to engage ledge portions 246 of second coupling portion 240 when corrective assembly 222 is urged against support assembly 220. In FIG. 28, the coupling portions are shown engaged to couple the support and corrective assemblies together to form an assembled appliance.

The strength of the engagement achieved with the coupling portions of this embodiment may relate to several factors, such as the material from which resilient fingers 252 are fabricated, as well as their shape, flexibility, degree of curvature, manner of attachment to peripheral edge 250 or flat surface 248, number, position, and so forth, all of which may be varied in other configurations of this embodiment.

Figure 29:
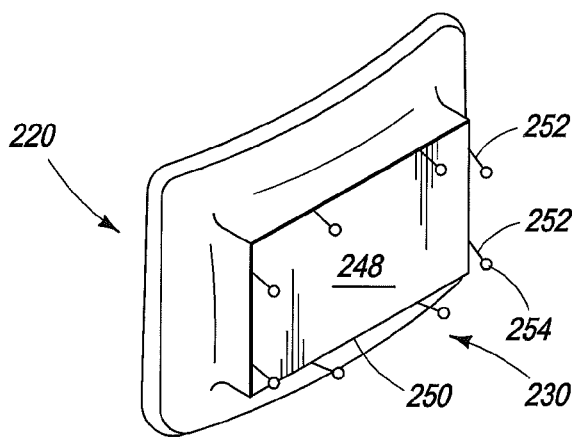
FIG. 29 is an isometric view of another configuration of the support assembly of FIG. 26.
Figure 30:
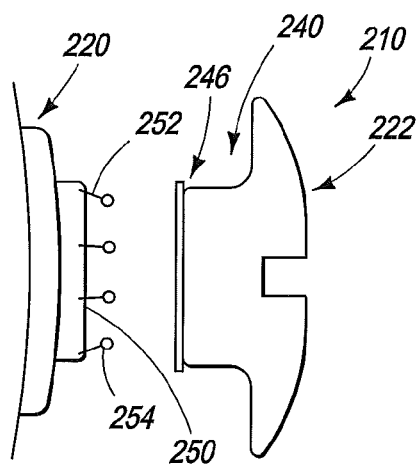
FIG. 30 is an exploded side elevation view of the support assembly of FIG. 29 with a corrective assembly.

For example, FIGS. 29 and 30 show another suitable configuration of support assembly 220 in which eight generally straight resilient fingers 252 are disposed on the sides of rectangular peripheral edge 250 on first coupling portion 230. Further, each finger 252 is slightly inclined toward the center of surface 248, and shown to terminate in a small sphere 254. Spheres 254 may assist in engaging ledge portions 246 when the assemblies are urged together, such as by providing a smooth surface along which the ledge portions may move as the assemblies are engaged (or disengaged). Spheres 254 may also retain the coupling portions in an engaged orientation. The number and/or placement of fingers 252 utilized in a particular embodiment may vary, such as with an embodiment including less than eight fingers, more than eight fingers, etc.

Figure 31:
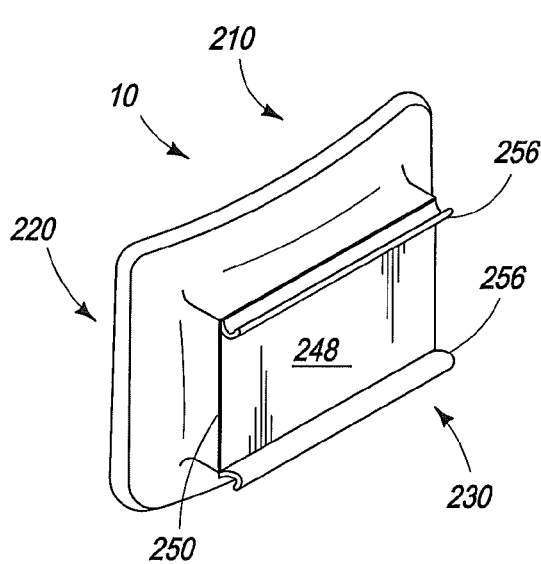
FIG. 31 is an isometric view of another configuration of the support assembly of FIG. 26.
Figure 32:
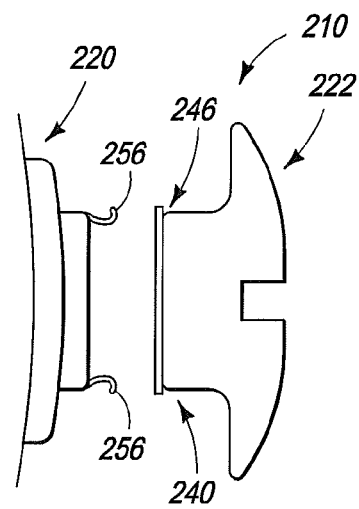
FIG. 32 is an exploded side elevation view of the support assembly of FIG. 31.

First coupling portion 230 may include any suitable structure adapted to engage ledge portions 246 of second coupling portion 240, instead of or in addition to resilient fingers 252. For example, FIG. 31 shows another suitable configuration of orthodontic appliance 210 in which first coupling portion 230 includes two outwardly curved ridge portions 256 disposed along two opposing sides of surface 248. Ridge portions 256 are shaped and positioned to engage two corresponding opposing ledge portions 246 on second coupling portion 240, which are shown in FIG. 32.

Ledge portions 246 may thus also be modified, for example to correspond more exactly to the structural components of first coupling portion 230 adapted to engage the ledge portions. For example, the ledge portions in FIGS. 26-32 are shown to be contiguous with respect to peripheral edge 244. However, other configurations may include intermittent ledge portions, disposed on peripheral edge 244 or elsewhere on first coupling portion 230 as desired, to engage the corresponding structure on first coupling portion 230.

Optionally, first and second coupling portions 230 and 240 may include structure adapted to correctly align corrective assembly 222 with support assembly 220, as described in greater detail above. Further, the coupling portions 230 and 240 may include one or more features to restrict or allow relative movement of the assemblies while engaged, for example by the configuration of the ledge portions 246 and/or the corresponding structural components of first coupling portion 230, and/or optionally by configuring the surfaces 242 and 248 to mate or interlock in some manner when the coupling portions are engaged. Moreover, some configurations of orthodontic appliance 210 may include a tether device and/or visual indicia to indicate incorrect engagement of the assemblies. Also, as with the embodiments disclosed above, the structure on first and second coupling portions may be inverted; in other words, first coupling portion 230 may include ledge portions 246, and the corresponding structural components to engage the ledge portions may be on second coupling portion 240.

Figure 33:
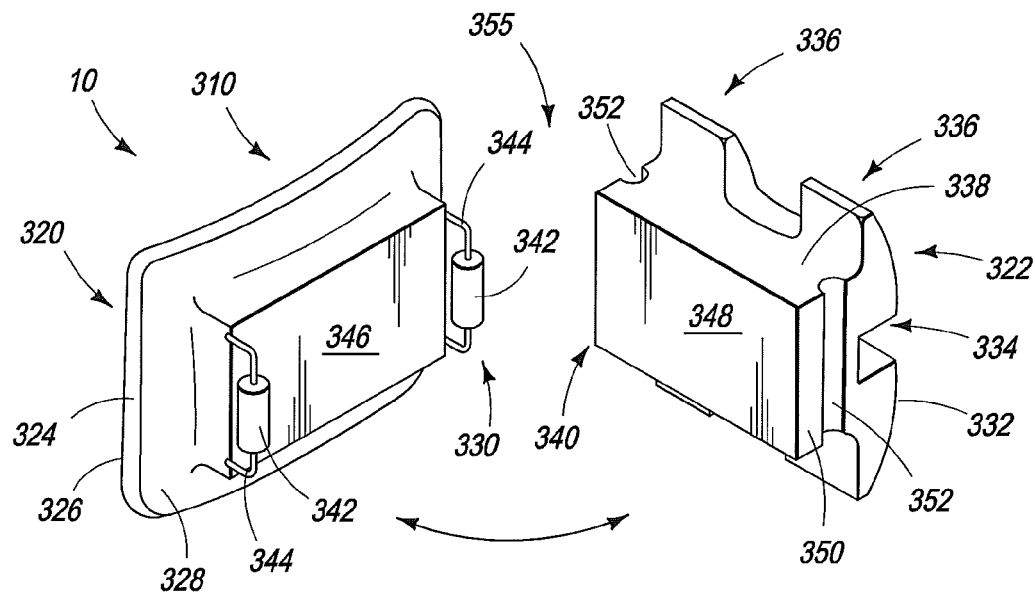
FIG. 33 is an exploded isometric view of another embodiment of a multi-piece, reusable orthodontic appliance according to the present disclosure.
Figure 34:
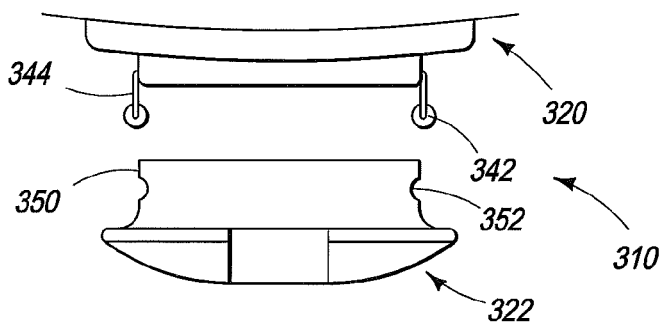
FIG. 34 is an exploded top plan view of the orthodontic appliance of FIG. 33.

Another illustrative example of an orthodontic appliance 10 according to the present disclosure is shown in FIGS. 33 and 34 and generally indicated at 310. In FIG. 33, orthodontic appliance 310 is shown to include a support assembly 320 and a corrective assembly 322. Support assembly 320 further includes a tooth engaging (or tooth-facing) portion 324 consisting of a tooth-facing rear surface 326, a support portion 328 in the form of a contoured pedestal-like structure, and a first coupling portion 330 disposed on the support portion. Corrective assembly 322 further includes a ligating-style wire engaging portion 332 that includes an archwire slot 334 and two pairs of tie wings 336. Corrective assembly 322 also includes a base portion 338 extending away from the wire engaging portion, and a second coupling portion 340 disposed on the base portion.

First coupling portion 330 is shown to include at least two sets of rollers 342 disposed on support frames 344 on opposing sides of a front surface 346, which as illustrated has a generally flat, rectangular configuration. Second coupling portion 340 is shown to include a corresponding rectangular surface 348 and four generally flat sides 350, two of which feature substantially semicircular grooves 352. The coupling portions may be described as forming portions of an engagement assembly 355. As shown in more detail in FIG. 34, grooves 352 are positioned and shaped to engage rollers 342 as the corrective assembly is urged against support assembly 320. As such, support frames 344 may be sufficiently flexible to be pushed slightly apart as sides 350 encounter rollers 342 when the assemblies are urged together and to hold rollers 342 within grooves 352 when the assemblies are engaged.

Other configurations of this embodiment may include variations in the disclosed structural features. For example, support frames 344 may support non-rotating, stationary ribs or other structure instead of or in addition to rollers 342. Surfaces 346 and 348 may be square in shape rather than rectangularly oblong as shown, with all four sides including support frames with rollers and/or corresponding grooves, for example to provide more than one possible orientation of corrective assembly 322 with support assembly 320. Optionally, as disclosed in greater detail above, first and second coupling portions 330 and 340 may be configured as desired to provide an alignment feature, movement restraining features, visual indicia, and so forth.

Another illustrative example of an orthodontic appliance 10 according to the present disclosure is shown in FIGS. 35-36. In FIG. 35, orthodontic appliance 410 is shown to include a support assembly 420 and a corrective assembly 422. Support assembly 420 further includes a tooth engaging (or tooth-facing) portion 424 consisting of a tooth-facing rear surface 426, a support portion 428 in the form of a contoured pedestal-like structure, and a first coupling portion 430 disposed on the support portion. Corrective assembly 422 further includes a ligating-style wire engaging portion 432 that includes an archwire slot 434 and two pairs of tie wings 436. Corrective assembly 422 also includes a base portion 438 extending away from the wire engaging portion, and a second coupling portion 440 disposed on the base portion.

First coupling portion 430 is shown to include a peripheral wall 442 bounding a cavity 444. As illustrated, cavity 444 has a rectangular configuration, but other shapes may be used. As shown in greater detail in FIG. 36, disposed in peripheral wall 442 are several bearings 446, each of which is biased toward cavity 444 by a spring 448. Bearings 446 may be retained in peripheral wall 442, such as by means of a retaining rim around the edge of the opening in wall 442 through which each bearing 446 protrudes.

Second coupling portion 440 is shown to include a generally rectangular surface 449, from which sides 450 extend to form a projection 452, the projection being sized and shaped to fit generally within cavity 444. Disposed on sides 450 are a plurality of detents 454, each of which is sized to receive a bearing 446.

Thus, coupling portions 430 and 440 may be engaged by urging corrective assembly 422 and support assembly 420 toward each other. As projection 452 encounters cavity 444, sides 450 depress bearings 446 within their respective openings until detents 454 are positioned to allow springs 448 to bias bearings 446 into the corresponding detents. The first and second coupling portions may be described as forming portions of an engagement assembly 455.

As disclosed in more detail above, different configurations of this embodiment may allow for alignment of the assemblies, restricted or permitted relative movement, and so forth.

Another illustrative example of an orthodontic appliance 10 according to the present disclosure is shown in FIGS. 37 and 38. In FIG. 37, orthodontic appliance 510 is shown to include a support assembly 520 and a corrective assembly 522. Support assembly 520 further includes a tooth engaging (or tooth-facing) portion 524 consisting of a tooth-facing rear surface 526, a support portion 528 in the form of a contoured pedestal-like structure, and a first coupling portion 530 disposed on the support portion. Corrective assembly 522 further includes a ligating-style wire engaging portion 532 that includes an archwire slot 534 and two pairs of tie wings 536. Corrective assembly 522 also includes a base portion 538 extending away from the wire engaging portion, and a second coupling portion 540 disposed on the base portion.

Appliance 510 includes an engagement assembly 555 that includes first and second coupling portions 530 and 540. First coupling portion 530 is shown to include a peripheral wall 542 and a floor 544 bounding a generally rectangular cavity 546. Disposed behind floor 544 are two magnets 548. Second coupling portion 540 is shown to include a surface 550 from which a generally rectangular projection 552 extends, terminating in a surface 554, the projection being sized and shaped to fit generally within cavity 546. Disposed behind surface 554 are two magnets 556, positioned to attract magnets 548 such that corrective assembly 522 may be releasably retained against support assembly 520 by means of the magnetic linkage established by magnets 548, 556.

In different configurations of this embodiment, the size, shape, strength, polarity and other characteristics of the magnetic forces exerted by magnets 548 and 556 may be varied to produce a desired bond strength. Further, the polarity, number, and positioning of magnets may provide an alignment feature and/or restrict relative movement of the engaged assemblies as described in greater detail above. In some configurations, magnets may be provided on only one coupling portion, with the other coupling portion including a magnetically responsive part, such as a component fabricated from or coated with, or otherwise including a magnetically active material. It is also within the scope of the present disclosure to include combinations of magnetic and magnetically responsive parts on both coupling portions. Some configurations may further include mechanical features as described in greater detail in the aforementioned embodiments. Further, any of the mechanical linkages described above may be provided with magnetic parts, alone or together with magnetically responsive parts, to achieve a desired bond character or strength.

Figure 40:
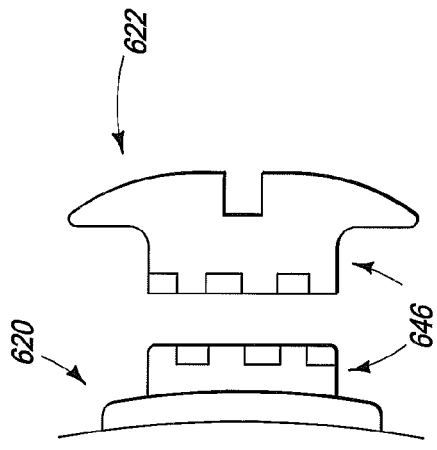
FIG. 40 is an exploded side elevation view of the orthodontic appliance of FIG. 39.
Figure 39:
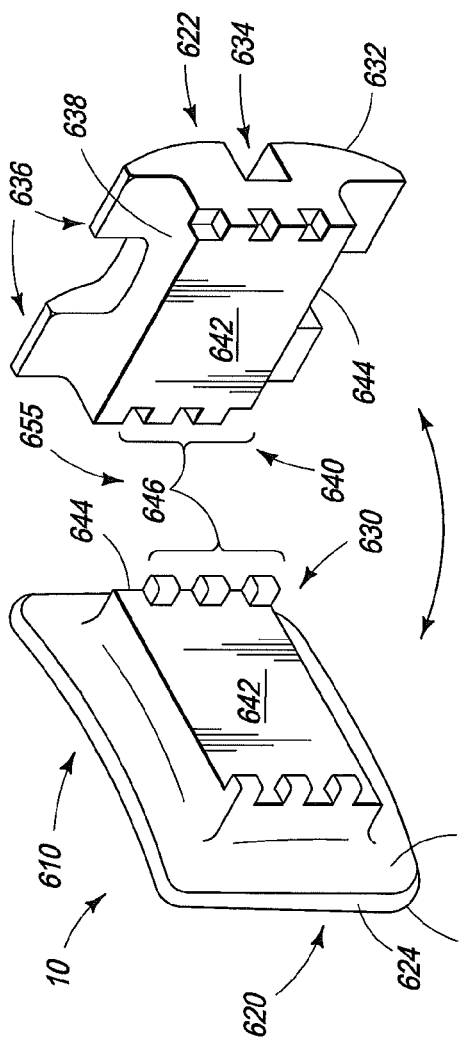
FIG. 39 is an exploded isometric view of another embodiment of a multi-piece, reusable orthodontic appliance according to the present disclosure.

Another illustrative example of an orthodontic appliance 10 according to the present disclosure is shown in FIGS. 39-40. In FIG. 39, orthodontic appliance 610 is shown to include a support assembly 620 and a corrective assembly 622. Support assembly 620 further includes a tooth engaging (or tooth-facing) portion 624 consisting of a tooth-facing rear surface 626, a support portion 628 in the form of a contoured pedestal-like structure, and a first coupling portion 630 disposed on the support portion. Corrective assembly 622 further includes a ligating-style wire engaging portion 632 that includes an archwire slot 634 and two pairs of tie wings 636. Corrective assembly 622 also includes a base portion 638 extending away from the wire engaging portion, and a second coupling portion 640 disposed on the base portion.

Appliance 610 includes an engagement assembly 655 that includes first and second coupling portions 630 and 640. First and second coupling portions 630 and 640 are each shown to include a generally rectangular surface 642 defined by a peripheral edge 644. Two opposing sides of each peripheral edge 644 are shown to include a series of interlock members 646, the interlock members of each coupling portion being positioned and sized to engage the interlock members of the other coupling portion when the portions are urged against each other. Although schematically depicted in FIG. 39 as having generally rectangular configurations, the interlock members may have any suitable shape, including spherical and other shapes. The interlock members may be primarily mechanical in nature, for example with friction holding the engaged portions together. Additionally or alternatively, the interlock members may be provided with magnetic parts and/or may further be adhesively bonded together (albeit with a lower-strength bond than is used to bond the support assembly to a tooth). It is within the scope of the present disclosure to include interlock members on more than two opposing sides of the edges and/or to include interlock members that extend from an internal, or non-perimeter, portion of the corresponding front and rear surfaces.

Figure 42:
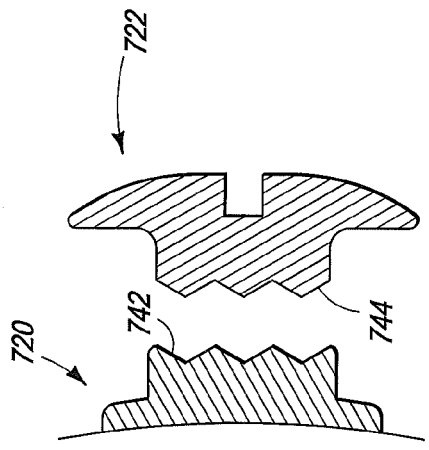
FIG. 42 is a cross section view of the orthodontic appliance of FIG. 41 along the lines 42-42 in FIG. 41.
Figure 41:
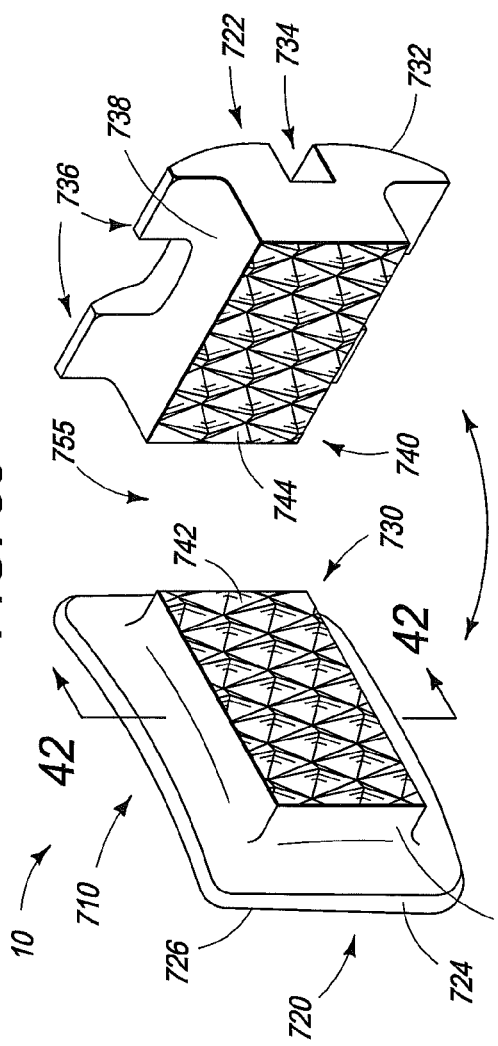
FIG. 41 is an exploded isometric view of another embodiment of a multi-piece, reusable orthodontic appliance according to the present disclosure.

Another illustrative example of an orthodontic appliance 10 according to the present disclosure is shown in FIGS. 41-42. In FIG. 41, orthodontic appliance 710 is shown to include a support assembly 720 and a corrective assembly 722. Support assembly 720 further includes a tooth engaging (or tooth-facing) portion 724 consisting of a tooth-facing rear surface 726, a support portion 728 in the form of a contoured pedestal-like structure, and a first coupling portion 730 disposed on the support portion. Corrective assembly 722 further includes a ligating-style wire engaging portion 732 that includes an archwire slot 734 and two pairs of tie wings 736. Corrective assembly 722 also includes a base portion 738 extending away from the wire engaging portion, and a second coupling portion 740 disposed on the base portion.

Appliance 710 includes an engagement assembly 755 that includes first and second coupling portions 730 and 740. First coupling portion 730 is shown to include a surface 742, and second coupling portion 740 is shown to include a corresponding surface 744. Surface 742 includes a three-dimensional pattern or texture to which surface 744 is complementarily shaped, so that the surfaces interlock when the coupling portions are urged together, as shown in FIG. 42.

In different configurations of this embodiment, the surface patterns and/or textures may be formed as desired, for example to achieve a desired amount of total surface area in contact when the coupling portions are engaged. Moreover, the surface material may be chosen to provide a desired friction coefficient. Optionally, the coupling portions may include other linkages as described above, such as mechanical, magnetic, adhesive, and so forth.

The embodiments described above are all shown to include a corrective assembly with a ligating wire engaging portion similar to that shown in FIGS. 4-5. However, as mentioned above, self-ligating wire engaging portions or other wire securing techniques may be used. Also, the embodiments are shown to include support and corrective assemblies with generally rectangular cross-sections, but differently shaped assemblies and assembly components may be used. Also, the embodiments described above illustrate coupling portions that are configured to engage when the corrective and support assemblies are urged together in a generally labial direction. However, to accommodate several considerations including tooth position and the nature of any forces to which an orthodontic appliance on the tooth may be subject, other configurations may include coupling portions configured to engage and disengage in any desired direction.

Some embodiments of orthodontic appliances 10 according to the present disclosure may be adapted for use with conventional orthodontic brackets that do not include a self-release mechanism for selectively and non-destructively disengaging an archwire-receiving corrective assembly of the bracket from a support assembly that couples the corrective assembly to a tooth. These conventional brackets are adapted to be attached directly to a tooth, and typically include a monolithic body member. When a force is imparted to these conventional orthodontic brackets, the most likely outcome is either that the bracket is debonded (i.e., removed) from the tooth or that the bracket resists being debonded and thereby conveys the force to the patient's tooth. As discussed previously, corrective assemblies 22 according to the present disclosure may include the ligating, self-ligating, and other structures of these conventional brackets. It is also within the scope of the present disclosure that orthodontic appliances 10 according to the present disclosure may be adapted to be used with and/or may include these conventional brackets, such as to retrofit these conventional brackets to include a self-release assembly according to the present disclosure. In such embodiments, the existing orthodontic bracket may be described as taking the place of the corrective assembly of an orthodontic appliance 10 according to the present disclosure. When used with a conventional orthodontic bracket, the orthodontic appliance 10 may include an engagement assembly 55 that is adapted to couple the bracket to a support assembly and to selectively disengage the bracket, and optionally at least a portion of the engagement assembly, from the support assembly, such as responsive to the above-described forces that otherwise might disengage the bracket from the tooth or impart undesirable forces to the tooth.

Figure 43:
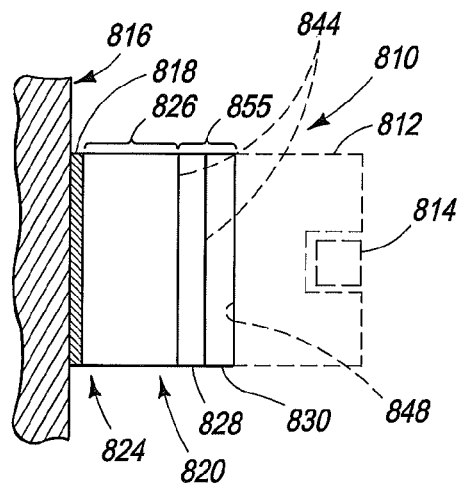
FIG. 43 is a schematic side elevation view showing various components of a multi-piece, reusable self-release assembly that is adapted for use with an orthodontic bracket that is adapted to be directly bonded to a tooth.

In FIG. 43, an example of an orthodontic appliance 10 according to the present disclosure that is adapted to be used with a corrective orthodontic bracket 812 is schematically illustrated and generally indicated at 810. As discussed, bracket 812 is adapted to receive an archwire 814 to impart corrective forces to a tooth, such as tooth 816, with the bracket including a rear surface 848 that is shaped or otherwise configured to be bonded directly to a tooth. Appliance 810 may be described as being a multi-piece, reusable self-release assembly 810 for use with corrective orthodontic bracket 812. Appliance, or self-release assembly, 810 is generally configured to be bonded to a tooth 816 via bonding media 818 and to be attached to corrective orthodontic bracket 812, which is adapted to receive archwire 814 to impart corrective forces to tooth 816. In particular, self-release assembly 810 includes a support assembly 820 and an engagement assembly 855. Support assembly 820 includes a tooth engaging (or tooth-facing) portion 824, which is adapted to be bonded or otherwise secured to tooth 816, and a support portion 826 extending from the tooth engaging portion and generally away from the tooth. As with the previously illustrated schematic examples, the relative sizes and thickness of the components of appliances 10 according to the present disclosure may vary without departing from the scope of the present disclosure. For example, in some embodiments, including the embodiment shown in FIG. 43, it may be desirable to utilize a support assembly that does not project from a tooth more than is necessary to provide the desired support and/or mounting structure, thereby reducing the distance to which the front surface of the archwire receiving surface of the appliance projects away from the tooth.

Engagement assembly 855 includes at least one coupling portion 830 that is adapted to be secured to bracket 812, such as the rear surface 848 of the bracket, with this portion being adapted to be releasably, or removably, engaged with either the front surface 844 of the support assembly and/or a corresponding coupling portion 828 of the engagement assembly, such as via any of the mechanisms described, illustrated and/or incorporated herein. Responsive to a sufficient force, at least portion 830 of the engagement assembly (and the attached bracket 812) is adapted to disengage from the support assembly (and/or portion 828). As such, the force will disengage the bracket from the support assembly, with engagement assembly 855 preventing the entirety of the force from being transmitted to the tooth or the debonding of support assembly 820. After disengagement, the bracket may be reengaged with the support assembly, such as by recoupling the engagement assembly. In other words, the bracket, support assembly, and engagement assembly are not destroyed or damaged during this disengagement and are adapted to be reused after disengagement.

In the illustrative example that is schematically illustrated in FIG. 43, engagement assembly 855 includes a first coupling portion 828 on the support portion of support assembly 820, and a second coupling portion 830 that is adapted to be attached to a corrective orthodontic bracket 812. Similar to structure of orthodontic appliance 10 as described above, the engagement assembly is adapted to releasably engage the first and second coupling portions and to disengage the first and second coupling portions responsive to a force applied to the orthodontic bracket that exceeds a predetermined value. Furthermore, the first coupling portion of the engagement assembly may be integrally formed with or otherwise secured to the support assembly, or alternatively, may be removably coupled to the support assembly.

Such a self-release assembly may be used, for example, with a suitable corrective orthodontic bracket, for example by attaching the second coupling portion of the self-release assembly to a base or bottom surface of an orthodontic bracket. The attachment of the second coupling portion to the orthodontic bracket may be done in any desired manner, such as by the use of adhesive and/or other suitable mechanism or linkage to achieve a desired bond. In such a manner, a set of conventional orthodontic brackets may be retrofitted or otherwise used with a set of self-release assemblies, to achieve a releasable engagement similar to that provided by the aforementioned orthodontic appliance 10 and the various embodiments illustrated herein. The engagement assembly, including either or both of the first and second coupling portions, may incorporate any of the features as described, illustrated and/or incorporated herein.

Figure 44:
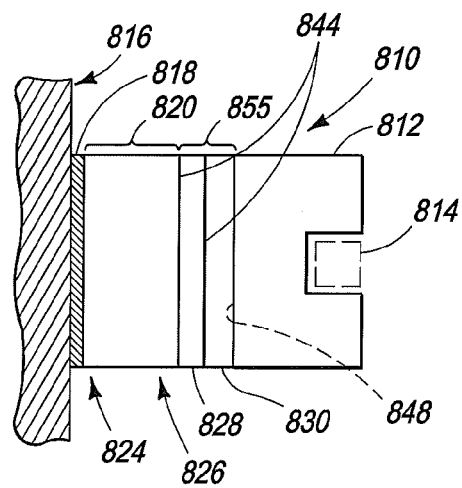
FIG. 44 is a schematic side elevation view of a multi-piece, reusable self-release assembly according to the present disclosure that includes an orthodontic bracket that may be bonded directly to a tooth when not used with the other portions of the assembly.

In FIG. 44, the schematic example of orthodontic appliance 810 of FIG. 43 is shown with the schematically depicted corrective bracket 812 shown in solid lines to graphically illustrate that it is within the scope of the present disclosure that orthodontic appliances according to the present disclosure may include corrective assemblies that are adapted to be separately used as corrective brackets that are bonded directly to a tooth. Described in slightly different terms, orthodontic appliances according to the present disclosure may include a conventional corrective bracket in addition to a multi-piece self-release assembly that includes a support assembly and an engagement assembly according to the present disclosure.

In a somewhat congruous manner, an alternative configuration of a self-release assembly may be adapted for use with an existing set of orthodontic hardware, except that installation of a self-release assembly may be performed without removing the hardware from the teeth. Instead, the self-release assembly may be configured to attach directly to the preinstalled hardware.

Figure 45:
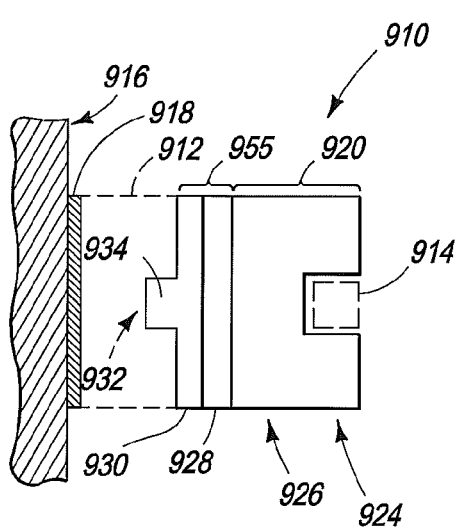
FIG. 45 is a diagram showing various components of an alternative configuration of a multi-piece, reusable self-release assembly for use with an orthodontic bracket that is directly bonded to a tooth.

For example, FIG. 45 is a diagram showing components of a multi-piece, reusable self-release assembly 910 for use with a corrective orthodontic bracket 912 engaged with an archwire 914 and bonded to a tooth 916 via bonding media 918. Self-release assembly 910 is generally configured to be attached to corrective orthodontic bracket 912 and receive or otherwise engage an archwire and transmit corrective forces from the archwire to the tooth.

In particular, self-release assembly 910 includes a corrective assembly 920 and an engagement assembly 955. Corrective assembly 920 includes a wire engaging portion 924 adapted to receive archwire 914 and a base portion 926 extending from the wire engaging portion and generally away from the archwire. Similar to self-release assembly 810, engagement assembly 955 includes a first coupling portion 928 on the base portion, and a second coupling portion 930 adapted to be attached to a corrective orthodontic bracket, such as may already be bonded to a tooth 916. The engagement assembly may be adapted to releasably engage the first and second coupling portions and to disengage the first and second coupling portions responsive to a force applied to the orthodontic bracket that exceeds a predetermined value.

This configuration of a self-release assembly may be used with a suitable corrective orthodontic bracket, for example by removing the archwire from the bracket and attaching the second coupling portion of the self-release assembly to the structure of the orthodontic bracket that previously engaged the archwire. More specifically, the second coupling portion of the engagement assembly should be configured to be secured to bracket 912, such as to the front surface thereof. As an illustrative example, if orthodontic bracket 912 is configured to engage an archwire via archwire slot 932, second coupling portion 930 may be provided with corresponding structure to fit within or otherwise accommodate archwire slot 932, such as a shaped protrusion 934 and/or any suitable structural components to establish a suitable connection with the conventional bracket. The attachment of the second coupling portion to the orthodontic bracket may be implemented in any desired manner, such as by the use of adhesive and/or other linkages to achieve a desired bond. It is not a requirement to all embodiments of such an assembly for the second coupling portion to be received within the wire receiving slot of the conventional bracket. After installation, archwire 914 may be engaged with corrective assembly 920 to resume orthodontic treatment.

It is within the scope of the present disclosure that a set of orthodontic appliances according to the present disclosure may include a plurality of support assemblies and a plurality of interchangeable corrective assemblies, the plurality of interchangeable corrective assemblies including corrective assemblies configured to direct corrective forces differently from each other. Such a set may allow an orthodontist to adjust the manner in which corrective forces are directed to a particular tooth, without removing the support assembly from the tooth, and without reshaping, replacing, or otherwise reconfiguring the archwire. Instead, the orthodontist may select from corrective assemblies that are configured to direct the corrective forces differently from each other, and exchange one for another when adjustment is desired. As described in more detail above, differentiation among corrective assemblies may be accomplished by appropriate differentiation in configuration of corrective assemblies, such as relative position and/or orientation of the archwire slot as shown, for example, in FIGS. 8-12.

Figure 46:
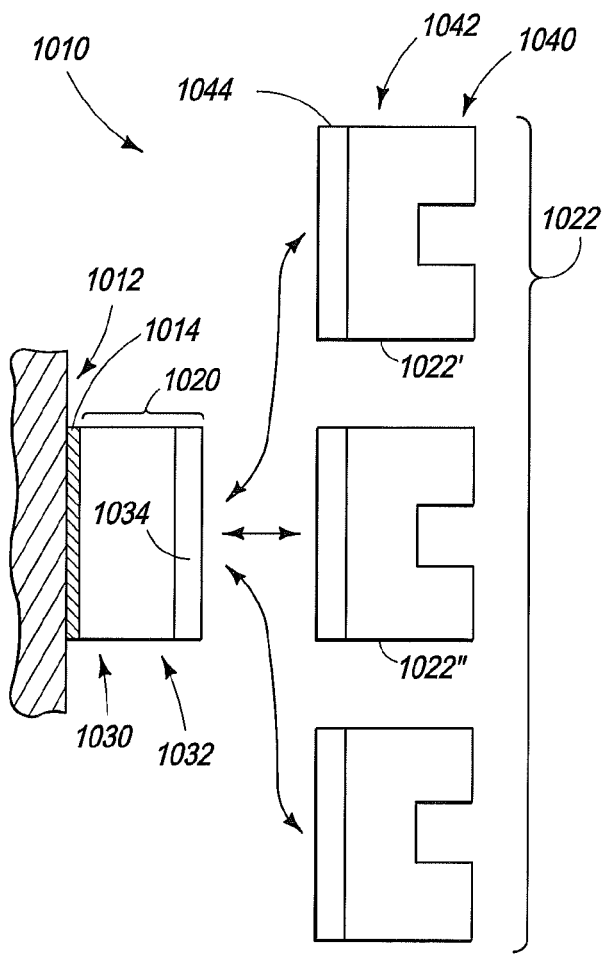
FIG. 46 is a diagram of a set of orthodontic appliances, represented as three interchangeable corrective assemblies and one support assembly.

Thus, FIG. 46 is a diagram showing components of a set 1010 of multi-piece, reusable orthodontic appliances generally configured to be bonded to a tooth 1012 via bonding media 1014, and more specifically to receive or otherwise engage an archwire (not shown) and transmit corrective forces from the archwire to the tooth. In particular, set 1010 includes at least one support assembly 1020 and a plurality of interchangeable corrective assemblies 1022. In FIG. 46, three corrective assemblies are shown for the purpose of illustration, but the number of such assemblies in a particular set may vary without departing from the scope of the present disclosure. As explained in greater detail above, each support assembly 1020 is adapted to bond to a tooth, and includes a tooth engaging (or tooth-facing) portion 1030 adapted to bond the support assembly to a tooth 1012, a support portion 1032 extending from the tooth engaging portion and generally away from the tooth, and a first coupling portion 1034 on the support portion. First coupling portion 1034 may be integrally formed with the support assembly or attached thereto. Each corrective assembly 1022 further includes a wire engaging portion 1040 that is adapted to receive an archwire, a base portion 1042 extending from the wire engaging portion and generally away from the archwire, and a second coupling portion 1044 on the base portion. Corrective assemblies 1022, by any appropriate means including those described above, may be configured to direct corrective forces differently with respect to each other. In other words, it is within the scope of the present disclosure for an orthodontist to change the corrective forces that are applied to a tooth merely be removing a first corrective assembly, such as assembly 1022' and replacing it with a second corrective assembly 1022", which is adapted to impart different corrective forces to the tooth than assembly 1022'. For example, the corrective assemblies may have different shapes, different thicknesses, different archwire receiving slots, etc. As explained above, the first and second coupling portions are configured to releasably engage the corrective assemblies with the support assembly. Therefore, while the plurality of corrective assemblies may be adapted to impart the same or different forces to a tooth, they should be similarly configured to be releasably engaged to the same or similarly shaped support assemblies.

Illustrative, non-exclusive, examples of descriptions of some orthodontic appliances within the scope of the present disclosure are presented in the following numbered paragraphs. The following paragraphs are not intended to be an exhaustive set of descriptions, and are not intended to define minimum or maximum scopes or required elements of the present disclosure. Instead, they are provided as illustrative examples of selected orthodontic appliances that are within the scope of the present disclosure, with other descriptions of broader or narrower scopes still being within the scope of the present disclosure.

1. An orthodontic appliance, comprising:
  a support assembly, comprising:
    a tooth engaging portion adapted to be bonded to a tooth;
    a support portion extending from the tooth engaging portion; and
    a first coupling portion on the support portion; and
  a corrective assembly adapted to direct corrective forces to at least the tooth to which the tooth engaging portion is bonded, the corrective assembly comprising:
    a wire engaging portion adapted to receive an archwire;
    a base portion extending from the wire engaging portion; and
    a second coupling portion on the base portion adapted to releasably engage the first coupling portion;
  wherein the first and second coupling portions are adapted to disengage responsive to a force applied to the corrective assembly that exceeds a predetermined value.

2. The orthodontic appliance of paragraph 1, wherein the predetermined value is less than a force sufficient to debond the support assembly from the tooth.

3. The orthodontic appliance of paragraphs 1-2, wherein one or both of the first and second coupling portions are adapted to prevent relative rotation of the portions when engaged.

4. The orthodontic appliance of paragraphs 1-3, wherein the support assembly further comprises visual indicia adapted to visually indicate if the first coupling portion is misaligned with the second coupling portion.

5. The orthodontic appliance of paragraph 4, wherein the visual indicia is visible when the first coupling portion is incorrectly engaged with the second coupling portion and obstructed from view when the second coupling portion is correctly engaged with the first coupling portion.

6. The orthodontic appliance of paragraphs 4-5, wherein the visual indicia comprises a distinctly colored surface on the first coupling portion.

7. The orthodontic appliance of paragraphs 1-6, further including a tether device adapted to limit the movement of the corrective assembly if the first coupling portion is disengaged from the second coupling portion.

8. The orthodontic appliance of paragraph 7, wherein the tether device comprises a hinge.

9. The orthodontic appliance of paragraph 8, wherein the hinge is biased toward a predetermined position.

10. The orthodontic appliance of paragraphs 1-9, wherein at least one of the first and second coupling portions is adapted to align the coupling portions in a predetermined relative orientation.

11. The orthodontic appliance of paragraphs 1-10, wherein at least one of the first and second coupling portions comprises a magnetically attractive part and the other of the first and second coupling portions comprises a part adapted to be attracted by the magnetic part.

12. The orthodontic appliance of paragraphs 1-11, wherein one of the first and second coupling portions includes a male part and the other of the first and second coupling portions includes a corresponding female part, and wherein the male part is adapted to engage the corresponding female part in a snap fit relationship.

13. The orthodontic appliance of paragraph 12, wherein one or both of the male and female parts are adapted to prevent relative rotation of the portions when engaged.

14. The orthodontic appliance of paragraphs 12-13, wherein the male and female parts have two-fold symmetry.

15. The orthodontic appliance of paragraph 12-14, wherein the first coupling portion further comprises at least one female part and the second coupling portion further comprises at least one corresponding female part, and wherein each male part is adapted to engage a corresponding female part.

16. The orthodontic appliance of paragraphs 1-15, wherein one of the first and second coupling portions comprises a surface defined by a peripheral edge, the peripheral edge having two or more resilient fingers that extend generally inward from the edge, and wherein the other of the first and second coupling portions comprises a corresponding surface defined by a peripheral edge, the peripheral edge having two or more ledge portions configured to be releasably engaged by the resilient fingers.

17. The orthodontic appliance of paragraph 16, wherein the fingers and ledge portions are adapted to prevent relative rotation of the first and second coupling portions when the ledges are engaged with the fingers.

18. The orthodontic appliance of paragraph 16 or 17, wherein the ledge portions are contiguous.

19. The orthodontic appliance of paragraph 16 or 17, wherein the ledge portions are spaced-apart from each other.

20. The orthodontic appliance of paragraphs 1-15, wherein one of the first and second coupling portions comprises a surface defined by a peripheral edge, the peripheral edge having two or more outwardly curved ridge portions, and wherein the other of the first and second coupling portions comprises a corresponding surface defined by a peripheral edge, the peripheral edge having one or more ledge portions configured to be releasably engaged by the ridge portions.

21. The orthodontic appliance of paragraphs 1-15, wherein one of the first and second coupling portions comprises a surface with at least two sides, at least two of the sides having a roller on a support frame projecting therefrom, and wherein the other of the first and second coupling portions comprises a surface with at least two sides, at least two of the sides having a groove configured to be releasably engaged by the rollers.

22. The orthodontic appliance of paragraphs 1-21, wherein one of the first and second coupling portions comprises a peripheral wall bounding a cavity, the wall having a plurality of bearings biased toward the center of the cavity, and wherein the other of the first and second coupling portions comprises a projection configured to fit substantially within the cavity, the projection having a plurality of detents configured to be releasably engaged by the bearings.

23. The orthodontic appliance of paragraphs 1-15, wherein the first and second coupling portions comprise surfaces with at least two sides, at least two of the sides having a series of spaced-apart interlock members, wherein the interlock members of each coupling portion are adapted to releasably interlock the interlock members of the other coupling portion when the coupling portions are urged together.

24. The orthodontic appliance of paragraphs 1-23, wherein the first and second coupling portions are adapted to be repeatedly engaged and disengaged without destruction of the coupling portions.

25. The orthodontic appliance of paragraphs 1-24, wherein, each of the support assembly and the corrective assembly are adapted to remain intact upon disengagement.

26. A self-release assembly for use with a corrective orthodontic bracket, the self-release assembly, comprising:
    a support assembly comprising a tooth engaging portion adapted to bond the support assembly to a tooth and a support portion extending from the tooth engaging portion; and
    an engagement assembly, comprising:
        a first coupling portion on the support portion; and
        a second coupling portion adapted to be attached to a corrective orthodontic bracket;
    wherein the engagement assembly is adapted to releasably engage the first and second coupling portions and to disengage the first and second coupling portions responsive to a force applied to the orthodontic bracket that exceeds a predetermined value.

27. The self-release assembly of paragraph 26, wherein the predetermined value is less than a force sufficient to debond the support assembly from the tooth.

28. The self-release assembly of paragraph 26 or 27, wherein the first and second coupling portions are adapted to be repeatedly engaged and disengaged without destruction of the first and the second coupling portions.

29. The self-release assembly of paragraphs 26-28, further including any permissible combination of subject matter recited in any one or more of paragraphs 2-25.

30. A self-release assembly for use with a corrective orthodontic bracket, the self-release assembly comprising:
a corrective assembly adapted to direct corrective forces to a tooth, the corrective assembly further comprising a wire engaging portion adapted to receive an archwire and a base portion extending from the wire engaging portion; and
an engagement assembly comprising:
a first coupling portion on the base portion; and
a second coupling portion adapted to be attached to a support assembly that is adapted to be coupled to a tooth;
wherein the engagement assembly is adapted to releasably engage the first and second coupling portions and to disengage the first and second coupling portions responsive to a force applied to the orthodontic bracket that exceeds a predetermined value.

31. The self-release assembly of paragraph 30, wherein the predetermined value is less than a force sufficient to debond the support assembly from the tooth.

32. The self-release assembly of paragraphs 30 or 31, wherein the first and second coupling portions are adapted to be repeatedly engaged and disengaged without destruction of the first and the second coupling portions.

33. The self-release assembly of paragraphs 30-32, further including any permissible combination of subject matter recited in any one or more of paragraphs 2-25.

34. A set of orthodontic appliances, comprising:
a plurality of support assemblies, each including:
a tooth engaging portion adapted to be bonded to a tooth;
a support portion extending from the tooth engaging portion; and
a first coupling portion on the support portion; and
a plurality of interchangeable corrective assemblies adapted to direct corrective forces to a tooth when coupled to a support assembly that is mounted on the tooth, wherein the plurality of interchangeable corrective assemblies includes at least a first corrective assembly and a second corrective assembly, wherein the first corrective assembly is configured to direct corrective forces differently from the second corrective assembly, and further wherein each corrective assembly comprises:
a wire engaging portion that is adapted to receive an archwire;
a base portion extending from the wire engaging portion; and
a second coupling portion on the base portion adapted to releasably engage the first coupling portion of one or more support assemblies;
wherein the first and second coupling portions are adapted to disengage responsive to a force applied to the corrective assembly that exceeds a predetermined value.

35. The set of paragraph 34, further including any permissible combination of subject matter recited in any one or more of paragraphs 2-25.

36. A method of orthodontic treatment of a tooth with the set of orthodontic appliances of paragraphs 35 or 36, the method comprising:
initiating orthodontic treatment by:
bonding the tooth engaging portion of a support assembly to a tooth;
engaging the first coupling portion of the support assembly with the second coupling portion on the first corrective assembly;
seating an archwire in the wire engaging portion; and
adjusting orthodontic treatment by:
disengaging the first and second coupling portions;
engaging the first coupling portion of the support assembly with the second coupling portion on the second corrective assembly.

37. A method of orthodontic treatment of a tooth with the set of orthodontic appliances that includes a plurality of support assemblies, which each are adapted to be bonded to a tooth and which each include a first coupling portion, and a plurality of interchangeable corrective assemblies, which each are adapted to direct corrective forces to a tooth when coupled to a support assembly that is bonded to the tooth, which each include a wire engaging portion that is adapted to receive an archwire and which each include a second coupling portion that is adapted to be selectively engaged with a first coupling portion on a support assembly of the plurality of support assemblies, the method comprising:
bonding a tooth engaging portion of a support assembly to a tooth;
engaging the first coupling portion of the support assembly with the second coupling portion of a first corrective assembly;
seating an archwire in the wire engaging portion; and
disengaging the first and second coupling portions; and
engaging the first coupling portion of the support assembly with a second coupling portion of a second corrective assembly.

38. A method of paragraphs 37, wherein the set includes the set of paragraph 35 or 36.

39. A method of adjusting corrective forces exerted by an archwire on a tooth, the method comprising:
securing a tooth engaging portion of a support assembly, which includes a support portion extending from the tooth engaging portion and a first coupling portion on the support portion, to a tooth;
selecting one of a plurality of corrective assemblies for directing corrective forces to the tooth, each corrective assembly comprising:
a wire engaging portion adapted to receive an archwire;
a base portion extending from the wire engaging portion; and
a second coupling portion on the base portion and configured to releasably engage the first coupling portion of the support assembly;
engaging the first coupling portion of the support assembly with the second coupling portion on the selected corrective assembly;
changing the corrective forces by:
disengaging the first and second coupling portions;
selecting another of the corrective assemblies configured to direct corrective forces differently from the previously engaged corrective assembly; and
engaging the first coupling portion of the support assembly with the second coupling portion on the selected corrective assembly.

40. A method of preventing unintentional debondment of an orthodontic appliance from a tooth, the method comprising:
bonding a tooth engaging portion of a support assembly to a tooth, the support assembly including a support portion extending from the tooth engaging portion and the support portion including a first coupling portion; and
engaging the first coupling portion with a second coupling portion on a corrective assembly of an orthodontic appliance, the corrective assembly including a wire engaging portion for receiving an archwire, the first and second coupling portions being configured to disengage responsive to a force applied to the orthodontic appliance that exceeds a predetermined value.

Although the various embodiments, configurations and methods of the present disclosure have been shown and described with reference to the foregoing operational principles and description, it will be apparent to those skilled in the art that various changes in form and detail may be made without departing from the spirit and scope of the disclosure.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. An orthodontic appliance, comprising:
   a support assembly, comprising:
      a tooth engaging portion adapted to be bonded to a surface of a tooth;
      a support portion extending from the tooth engaging portion; and
      a first coupling portion on the support portion;
   a corrective assembly adapted to direct corrective forces to at least the tooth to which the tooth engaging portion is bonded, the corrective assembly comprising:
      a wire engaging portion adapted to receive an archwire;
      a base portion extending from the wire engaging portion; and
      a second coupling portion on the base portion and releasably engaged with the first coupling portion, wherein, when the first and second coupling portions are operatively engaged with each other, the first and second coupling portions are adapted to disengage, without destruction of either of the first and second coupling portions, responsive to a force that exceeds a predetermined value and which is less than a force required to debond the support portion from the surface of the tooth; and
   a tether device that interconnects the corrective assembly with the support assembly, wherein the tether device is adapted to limit relative movement of the corrective assembly with respect to the support assembly when the corrective assembly is disengaged from the support assembly; wherein the tether device includes a hinge mechanism that connects the first and second coupling portions of the corrective and support assemblies.

2. The orthodontic appliance of claim 1, wherein the tether device is adapted to limit movement of the corrective assembly from the support assembly when the corrective assembly is disengaged from the support assembly by the force.

3. The orthodontic appliance of claim 1, wherein the tether device is adapted to couple the corrective assembly with the support assembly even when the corrective assembly is disengaged from the support assembly.

4. The orthodontic appliance of claim 1, wherein the hinge mechanism is configured to align the corrective assembly with the support assembly.

5. The orthodontic appliance of claim 1, wherein the hinge mechanism is adapted to restrict relative movement of the corrective assembly and the support assembly when the corrective assembly is engaged with the corrective assembly.

6. The orthodontic appliance of claim 1, wherein the hinge mechanism includes a biasing member.

7. The orthodontic appliance of claim 6, wherein the biasing member biases the corrective assembly into alignment with the support assembly.

8. The orthodontic appliance of claim 1, wherein the first and second coupling portions are configured to permit relative movement of the corrective assembly and the support assembly when the corrective assembly is coupled to the support assembly.

9. The orthodontic appliance of claim 1, wherein, the force for disengagement is applied to the corrective assembly in a direction other than from the support assembly to the corrective assembly.

10. The orthodontic appliance of claim 1, wherein, the force for disengagement is at least one of a peel force and a sheer force.

11. The orthodontic appliance of claim 1, wherein the corrective assembly is a self-ligating corrective assembly.

12. The orthodontic appliance of claim 11, wherein the self-ligating corrective assembly includes a self-locking mechanism that is adapted to retain an archwire within the wire engaging portion without requiring ligatures.

13. The orthodontic appliance of claim 12, wherein the self-locking mechanism includes a locking structure that is configured to releasably secure an archwire within the wire engaging portion.

14. The orthodontic appliance of claim 1, wherein one or both of the first and second coupling portions are adapted to prevent relative rotation of the coupling portions when engaged.

15. The orthodontic appliance of claim 1, wherein at least one of the first and second coupling portions is adapted to align the coupling portions in a predetermined relative orientation.

16. The orthodontic appliance of claim 1, wherein the first and second coupling portions are adapted to be repeatedly engaged and disengaged without destruction of the coupling portions, and further wherein each of the support assembly and the corrective assembly are adapted to remain intact upon disengagement of the first and second coupling portions.

17. The orthodontic appliance of claim 1, wherein the support assembly further comprises visual indicia adapted to visually indicate if the first coupling portion is misaligned with the second coupling portion, and further wherein the visual indicia is visible when the first coupling portion is incorrectly engaged with the second coupling portion and obstructed from view when the second coupling portion is correctly engaged with the first coupling portion.

18. The orthodontic appliance of claim 1, wherein one of the first and second coupling portions includes a male part and the other of the first and second coupling portions includes a corresponding female part, and wherein the male part is adapted to engage the corresponding female part in a snap fit relationship.

19. The orthodontic appliance of claim 18, wherein the male part extends from the corrective assembly, and further wherein when the first and second coupling portions are operatively engaged, the male part extends toward the tooth engaging portion.

20. The orthodontic appliance of claim 18, wherein the male part extends from the support assembly, and further wherein when the first and second coupling portions are operatively engaged, the male part extends away from the tooth engaging portion.

21. The orthodontic appliance of claim 1, wherein the support assembly does not include a wire engaging portion adapted to receive an archwire.

22. The orthodontic appliance of claim 1, wherein when the first and second coupling portions are operatively engaged with each other, the wire engaging portion extends farther from the surface of the tooth relative to the first and second coupling portions.

23. The orthodontic appliance of claim 1, wherein when the first and second coupling portions are operatively engaged with each other, the first and second coupling portions extend between the wire engaging portion and the tooth engaging portion.

24. The orthodontic appliance of claim 1, wherein when the first and second coupling portions are operatively engaged with each other, the base portion and the support portion extend between the wire engaging portion and the tooth engaging portion.

* * * * *